US012669505B2

(12) United States Patent
Carter et al.

(10) Patent No.: US 12,669,505 B2
(45) Date of Patent: Jun. 30, 2026

(54) DETECTION OF DESMOGLEIN-2 IN CANCERS OF EPITHELIAL ORIGIN

(71) Applicants: HDT Bio Corp., Seattle, WA (US); University of Washington, Seattle, WA (US)

(72) Inventors: Darrick Carter, Seattle, WA (US); Jiho Kim, Seattle, WA (US); Andre Lieber, Seattle, WA (US)

(73) Assignees: HTD Bio Corp., Seattle, WA (US); University of Washington, Seattle, WA (US)

( * ) Notice: Subject to any disclaimer, the term of this patent is extended or adjusted under 35 U.S.C. 154(b) by 970 days.

(21) Appl. No.: 17/715,092

(22) Filed: Apr. 7, 2022

(65) Prior Publication Data

US 2022/0229061 A1 Jul. 21, 2022

Related U.S. Application Data

(63) Continuation of application No. PCT/US2020/054830, filed on Oct. 8, 2020.

(60) Provisional application No. 62/913,071, filed on Oct. 9, 2019.

(51) Int. Cl.
| | |
|---|---|
| *G01N 33/57545* | (2026.01) |
| *A61K 45/06* | (2006.01) |
| *G01N 27/447* | (2006.01) |
| *G01N 33/543* | (2006.01) |

(52) U.S. Cl.
CPC ....... *G01N 33/57545* (2026.01); *A61K 45/06* (2013.01); *G01N 27/44739* (2013.01); *G01N 33/543* (2013.01); *G01N 2333/47* (2013.01)

(58) Field of Classification Search
CPC ................................................ G01N 33/57449
USPC ........................................................ 435/7.23
See application file for complete search history.

(56) References Cited

U.S. PATENT DOCUMENTS

| | | | |
|---|---|---|---|
| 5,527,773 | A | 6/1996 | Steinert |
| 6,169,071 | B1 | 1/2001 | Blaschuk |
| 6,245,888 | B1 | 6/2001 | Staddon |
| 6,407,058 | B1 | 6/2002 | Staddon |
| 6,455,314 | B1 | 9/2002 | Wickham |
| 7,560,527 | B1 | 7/2009 | Legrand |
| 8,722,853 | B2 | 5/2014 | Lieber |
| 2002/0016876 | A1 | 2/2002 | Farmwald |
| 2002/0127198 | A1 | 9/2002 | Rothbard |
| 2004/0038924 | A1 | 2/2004 | Davidson |
| 2004/0229811 | A1 | 11/2004 | Blaschuk |
| 2005/0119455 | A1 | 6/2005 | Fuh |
| 2005/0181375 | A1 | 8/2005 | Aziz |
| 2006/0006792 | A1 | 1/2006 | Strip |
| 2006/0025166 | A1 | 2/2006 | Dang |
| 2006/0067927 | A1 | 3/2006 | Chandrasekaran |
| 2006/0251663 | A1 | 11/2006 | Mariscal-Gonzalez |
| 2008/0124360 | A1 | 5/2008 | Seggern |
| 2008/0125364 | A1 | 5/2008 | Nusrat |
| 2011/0305634 | A1 | 12/2011 | Lieber |
| 2014/0107014 | A1 | 4/2014 | Lieber |
| 2015/0246949 | A1 | 9/2015 | Lieber |
| 2016/0257721 | A1 | 9/2016 | Lieber |
| 2017/0037431 | A1 | 2/2017 | Lieber |

FOREIGN PATENT DOCUMENTS

| | | |
|---|---|---|
| CN | 101068933 A | 11/2007 |
| WO | 199104745 W | 4/1991 |
| WO | 9914359 W | 3/1999 |
| WO | 0042208 W | 7/2000 |
| WO | 2005040333 A2 | 5/2005 |
| WO | 2005116259 | 12/2005 |
| WO | 2006133361 | 12/2006 |
| WO | 2008057545 | 5/2008 |
| WO | 2013003384 | 1/2013 |

OTHER PUBLICATIONS

Barber et al (PLOS One, 2014, 9(6)(e98786): 1-10).*
Tockman et al (Cancer Res., 1992, 52:2711s-2718s).*
Cai et al (J Cancer Res Clin Oncol, 2017, 143: 59-69).*
Nava et al (Molecular Biology of the Cell, 2007, 18: 4565-4578).*
Harada et al (Cancer Sci, 2003, 94(4): 394-399).*
Lowe (PLOS Computational Biology, 2017, e1005457, 1-23).*
Wang et al (Drug Delivery, 2016, 23(4): 1398-1403).*
Han et al (European Review for Medical Pharmacological Sciences, 2018, 22: 5481-5489).*
Abbod, M. F., et al., Predictive modeling in cancer: where systems biology meets the stock market. Expert Rev Anticancer Ther. Jul. 2009;9(7):867-70.
Adams, G. P., et al. "Monoclonal antibody therapy of cancer," Nat Biotechnol. Sep. 2005;23(9):1147-57. doi: 10.1038/nbt1137.
Adams, P. D., et al., "PHENIX: a comprehensive Python-based system for macromolecular structure solution" Acta Crystallogr D Biol Crystallogr. Feb. 2010;66(Pt 2):213-21. doi: 10.1107/S0907444909052925.
Amberg, N., "Adenovirus receptors: implications for tropism, treatment and targeting," Rev Med Virol. May 2009;19(3):165-78. doi: 10.1002/rmv.612.
Amieva, M. R., et al. "Disruption of the Epithelial Apical-Junctional Complex by Helicobacter pylori CagA," Science. May 30, 2003;300(5624):1430-4. doi: 10.1126/science.1081919.
Andarawewa, K. L., et al. "Ionizing Radiation Predisposes Non-malignant Human Mammary Epithelial Cells to Undergo Transforming Growth Factor b-Induced Epithelial to Mesenchymal Transition," Cancer Res. Sep. 15, 2007;67(18):8662-70. doi: 10.1158/0008-5472.CAN-07-1294.
Beatty, M. S., et al. "Adenovirus Strategies for Tissue-Specific Targeting." Adv Cancer Res. 2012;115:39-67. doi: 10.1016/B978-0-12-398342-8.00002-1.

(Continued)

*Primary Examiner* — Sean E Aeder

(74) *Attorney, Agent, or Firm* — Greenberg Traurig, LLP

(57) ABSTRACT

The disclosure provides methods of diagnosing, prognosing and stratifying cancers in a patient, comprising detecting elevated expression of desmoglein-2 (DSG-2) in a sample of the cancer and referencing that level to historic data to determine treatment regimen, stage, and prognosis of a patient.

11 Claims, 8 Drawing Sheets

(56)                    References Cited

OTHER PUBLICATIONS

Beckhove, P., et al. "Specifically activated memory T cell subsets from cancer patients recognize and reject kenotransplanted autologous tumors" J Clin Invest. Jul. 2004;114(1):67-76. doi: 10.1172/JCI20278.

Belousova, N., et al., "Modification of Adenovirus Capsid with a Designed Protein Ligand Yields a Gene Vector Targeted to a Major Molecular Marker of Cancer" J Virol. Jan. 2008;82(2):630-7. doi: 10.1128/JVI.01896-07.

Bergelson, J. M., et al. "Isolation of a Common Receptor for Coxsackie B Viruses and Adenoviruses 2 and 5," Science. Feb. 28, 1997;275(5304):1320-3. doi: 10.1126/science.275.5304.1320 (Abstract only).

Bewley, M. C., et al., "Structural Analysis of the Mechanism of Adenovirus Binding to its Human Cellular Receptor, CAR" Science. Nov. 19, 1999;286(5444):1579-83. doi: 10.1126/science.286.5444.1579.

Getsios, S. P., et al. "Working out the Strength and Flexibility of Desmosomes," Nat Rev Mol Cell Biol. Apr. 2004;5(4):271-81. doi: 10.1038/nrm1356.

Beyer, I., et al. "Controlled Extracellular Matrix Degradation in Breast Cancer Tumors Improves Therapy by Trastuzumab," Mol Ther. Mar. 2011;19(3):479-89. doi: 10.1038/mt.2010.256.

Beyer, I., et al., "Co-administration of epithelial junction opener JO-1 improves the efficacy and safety of chemotherapeutic drugs" Clin Cancer Res. Jun. 15, 2012;18(12):3340-51. doi: 10.1158/1078-0432.CCR-11-3213.

Beyer, I., et al., "Epithelial junction opener JO-1 improves monoclonal antibody therapy of cancer" Cancer Res. Nov. 15, 2011;71(22):7080-90. doi: 10.1158/0008-5472.CAN-11-2009.

Biedermann, K., et al. "Desmoglein 2 is expressed abnormally rather than mutated in familial and sporadic gastric cancer" J Pathol. Oct. 2005;207(2):199-206. doi: 10.1002/path.1821.

Bostrom, J., et al. "Variants of the Antibody Herceptin That Interact with HER2 and VEGF at the Antigen Binding Site," Science. Mar. 20, 2009;323(5921):1610-4. doi: 10.1126/science.

Brennan, K., et al. "Tight Junctions: A Barrier to the Initiation and Progression of Breast Cancer?" J Biomed Biotechnol. 2010;2010:460607. doi: 10.1155/2010/460607.

Cadwell, R. C., et al., "Mutagenic PCR," PCR Methods Appl. Jun. 1994;3(6):S136-40. doi: 10.1101/gr.3.6.s136.

Cadwell, R. C., et al., "Randomization of Genes by PCR Mutagenesis" PCR Methods Appl. Aug. 1992;2(1):28-33. doi: 10.1101/gr.2.1.282.

Campos, S. K., et al., "Avidin-based targeting and purification of a protein IX-modified, metabolically biotinylated adenoviral vector" Mol Ther. Jun. 2004;9(6):942-54. doi: 10.1016/j.ymthe.2004.03.006.

Carr, M. J., et al., "Deaths Associated with Human Adenovirus-14p1 Infections, Europe, 2009-2010" Emerg Infect Dis. Aug. 2011;17(8):1402-8. doi: 10.3201/eid1708.101760. PMID: 21801616.

Chitaev, N. A., et al. "Direct Ca2+-dependent Heterophilic Interaction between Desmosomal Cadherins, Desmoglein and Desmocollin, Contributes to Cell-Cell Adhesion," J Cell Biol. Jul. 14, 1997;138(1):193-201. doi: 10.1083/cb.138.1.193.

Cowin, P., "Unraveling the cytoplasmic interactions of the cadherin superfamily," Proc Natl Acad Sci U S A. Nov. 8, 1994;91(23):10759-61. doi: 10.1073/pnas.91.23.10759.

Coyne, C. B., et al. "CAR: A virus receptor within the tight junction," Adv Drug Deliv Rev. Apr. 25, 2005;57(6):869-82. doi: 10.1016/j.addr.2005.01.007.

Coyne, C. B., et al. "Coxsackievirus Entry across Epithelial Tight Junctions Requires Occludin and the Small GTPases Rab34 and Rab5", Cell Host Microbe. Sep. 13, 2007;2(3):181-92. doi: 10.1016/j.chom.2007.07.003.

Cupelli, K., et al., "Structure of Adenovirus Type 21 Knob in Complex with CD46 Reveals Key Differences in Receptor contacts among Species B Adenoviruses," J Virol. Apr. 2010;84(7):3189-200. doi: 10.1128/JVI.01964-09.

Cuppelli, K., et al., "Viral attachment strategies: the many faces of adenoviruses" Curr Opin Virol. Aug. 2011;1(2):84-91. doi: 10.1016/j.coviro.2011.05.024.

Decrescenzo, et al., "Real-Time Monitoring of the Interactions of Two-Stranded de NoVo Designed Coiled-Coils: Effect of Chain Length on the Kinetic and Thermodynamic Constants of Binding", Biochem. 42: 1754-1763 (2003).

Di Guilmi, A. M., et al. "Human adenovirus serotype 3 (Ad3) and the Ad3 fiber protein bind to a 130-kDa membrane protein on Hela cells" Virus Res. Sep. 1995;38(1):71-81. doi: 10.1016/0168-1702(95)00043-p.

Disis, M. L., "Enhancing Cancer Vaccine Efficacy via Modulation of the Tumor Microenvironment," 2009. Clin Cancer Res 15:6476-6478.

Disis, M. L., et al. "Existent T-Cell and Antibody Immunity to HER-2/neu Protein in Patients with Breast Cancer" Cancer Res. Jan. 1, 1994;54(1):16-20.

Disis, M. L., et al. "Pre-existent immunity to the HER-2/neu oncogenic protein in patients with HER-2/neu overexpressing breast and ovarian cancer" Breast Cancer Res Treat. Aug. 2000;62(3):245-52. doi: 10.1023/a:1006438507898.

Durmort, C., et al., "Structure of the Fiber Head of Ad3, a Non-CAR-Binding Serotype of Adenovirus," Virology. Jul. 5, 2001;285(2):302-12. doi: 10.1006/viro.2001.0967.

Emsley, P., et al., "Features and development of Cool" Acta Crystallogr D Biol Crystallogr. Apr. 2010; 66(Pt 4):486-501. doi: 10.1107/S0907444910007493.

Esposito, D. H., et al., "Outbreak of Pneumonia Associated with Emergent Human Adenovirus Serotype 14—Southeast Alaska, 2008" The Journal of Infectious Diseases, vol. 202, Issue 2, Jul. 15, 2010, pp. 214-222, https://doi.org/10.1086/653498.

Fasano, A., et al. "Vibrio cholerae produces a second enterotoxin, which affects intestinal tight junctions" Proc Natl Acad Sci U S A. Jun. 15, 1991;88(12):5242-6. doi: 10.1073/pnas.88.12.5242.

Fender, et al. "Synthesis, cellular localization, and quantification of penton-dodecahedron in serotype 3 adenovirus-infected cells, " Virology. Sep. 30, 2005;340(2):167-73. doi: 10.1016/j.virol.2005.06.030Fe.

Fender, P. A., et al. "Adenovirus dodecahedron, a new vector for human gene transfer" Proc Natl Acad Sci U S A. Jun. 15, 1991;88(12):5242-6. doi: 10.1073/pnas.88.12.5242.

Fessler, S. P., et al. "MUC1* is a determinant of trastuzumab (Herceptin) resistance in breast cancer cells" Breast Cancer Res Treat. Nov. 2009;118(1):113-24. doi: 10.1007/s10549-009-0412-3.

Feuerer, M., et al. "Therapy of human tumors in NOD/SCID mice with patient derived reactivated memory T cells from bone marrow" Nat Med. Apr. 2001;7(4):452-8. doi: 10.1038/86523.

Fleischli, C., et al. "Species B adenovirus serotypes 3, 7, 11 and 35 share similar binding sites on the membrane cofactor protein CD46 receptor" J Gen Virol. Nov. 2007;88(Pt 11):2925-2934. doi: 10.1099/vir.0.83142-0.

Frank, C. F., et al. "Cleavage of E-cadherin: a mechanism for disruption of the intestinal epithelial barrier by Candida albicans," Transl Res. Apr. 2007;149(4):211-22. doi: 10.1016/j.trsl.2006.11.006.

Fuschiotti, P. et al. "Structure of the Dodecahedral Penton Particle from Human Adenovirus Type 3" J Mol Biol. Feb. 17, 2006;356(2):510-20. doi: 10.1016/j.jmb.2005.11.048.

Gaggar, , et al. "Identifying Functional Adenovirus-Host Interactions Using Tandem Mass Spectrometry" Methods Mol Med. 2007;131:141-55. doi: 10.1007/978-1-59745-277-9_11.

Gaggar, A., et al. "The Human Membrane Cofactor CD46 is a Receptor for Species B Adenovirus Serotype 3" Nat Med. Nov. 2003;9(11):1408-12. doi: 10.1038/nm952.

Gao, W., et al. "Human adenovirus type 35: nucleotide sequence and vector development," Gene Ther 10, 1941-1949 (2003). https://doi.org/10.1038/sj.gt.3302097.

GenBank: AAP31205.1. fiber [Human adenovirus B3]. Dated Jun. 19, 2003. https://www.ncbi.nlm.nih.gov/protein/32127278?report=genbank&log$=protalign&blast_rank=7&RID=XK79G68Z01 R.

GenBank: ABB17809.1. L5 protein IV (fiber) [Human adenovirus B3]. Dated Nov. 3, 2005. https://www.ncbi.nlm.nih.gov/protein/ABB17809.1.

(56) References Cited

OTHER PUBLICATIONS

Nava, P., et al. "Desmoglein-2: A Novel Regulator of Apoptosis in the Intestinal Epithelium," Mol Biol Cell. Nov. 2007;18(11):4565-78. doi: 10.1091/mbc.e07-05-0426.

Ni, S., et al. "Evaluation of adenovirus vectors containing serotype 3 5 fibers for tumor targeting" Cancer Gene Ther. Dec. 2006;13(12):1072-81. doi: 10.1038/sj.cgt.7700981.

Norrby, E., et al. "Separation and Characterization of Soluble Adenovirus Type 9 Components" J Virol. Dec. 1967;1(6):1101-8. doi: 10.1128/JVI.1.6.1101-1108.1967.

Oliveras-Ferraros, C., et al. "Stem Cell Property Epithelial-to Mesenchymal Transition is a Core Transcriptional Network for Predicting Cetuximab (ErbituxTM) Efficacy in KRAS Wild-Type Tumor Cells" J Cell Biochem. Jan. 2011;11 (1):10-29.

Pache, L., et al., "Conservation of fiber structure and CD46 usage by subgroup B2 adenoviruses," Virology. Jun. 5, 2008;375(2):573-9. doi: 10.1016/j.virol.2008.02.013.

PDB: 1 H7Z_A. Chain A, Adenovirus Ad3 Fibre Head. Dated Oct. 10, 2012; https://www.rcsb.org/structure/1HZA.

PDB: 4LIY A. Chain A. Structure of the Adenovirus 3 Knob domain K217e and F224s Mutant. Dated May 28, 2014; https://www.rcsb.org/structure/4LIY.

Persson, B. D., et al. "Adenovirus type 11 binding alters the conformation of its receptor CD46," Nat Struct Mol Biol. Feb. 2007;14(2):164-6. doi: 10.1038/nsmb1190.

Persson, B. D., et al. "An Arginine Switch in the Species B Adenovirus Knob Determines High-Affinity Engagement of Cellular Receptor CD46"J Virol. Jan. 2009;83(2):673-86. doi: 10.1128/JVI.01967-08.

Pitner Ragan et al: "Structure-based Design of JOC-x, a Conjugatable Tumor Tight Junction Opener to Enhance Cancer Therapy", Scientific Reports, vol. 9, No. 1, Apr. 16, 2019 (Apr. 16, 2019), XP055871741, DOI: 10.1038/s41598-019-42229-3.

Ramani, V., et al. "Desmoglein 2 is a substrate of kallikrein 7 in pancreatic cancer" BMC Cancer. Dec. 17, 2008;8:373. doi: 10.1186/1471-2407-8-373.

Ranki, T., et al., "Serotype Chimeric Human Adenoviruses for Cancer Gene Therapy", Viruses. Oct. 2010;2 (10):2196-212. doi: 10.3390/v2102196.

Richter, Maximilian et al: "Preclinical safety and efficacy studies with an affinity-enhanced epithelial junction opener and PEGylated liposomal doxorubicin" , Molecular Therapy—Methods & Clinical Development, vol. 2, Jan. 1, 2015 (Jan. 1, 2015), p. 15005, XP055875000.

Sakamoto, M., et al. "Longitudinal Investigation of Epidemiologic Feature of Adenovirus Infections in Acute Respiratory Illnesses among Children in Yamagata, Japan (1986-1991)," Tohoku J Exp Med. Mar. 1995;175(3):185-93. doi: 10.1620/tjem.175.185.

Sanchez, M. P., et al. "Outbreak of Adenovirus 35 Pneumonia among Adult Residents and Staff of a Chronic Care Psychiatric Facility," J Infect Dis. Sep. 1997;176(3):760-3. doi: 10.1086/517295.

Schafer, S., et al. "Identification of the Ubiquitous Human Desmoglen, Dsg2, and the Expression of Catalogue of the Desmoglein Subfamily of Desmosomal Cadherins" Exp Cell Res. Apr. 1994;211(2):391-9. doi: 10.1006/excr.1994.1103.

Schlegel, N., et al., "Desmoglein 2-mediated adhesion is required for intetinal epithelial barrier integrity," Am J Physiol Gastrointest Liver Physiol. May 2010;298(5):G774-83. doi: 10.1152/ajpgi.00239.2009.

Scmitt, C. J., et al. "Homo- and Heterotypic Cell Contacts in Malignant Melanoma Cells and Desmoglein 2 as a Novel Solitary Surface Glycoprotein" J Invest Dermatol. Sep. 2007;127(9):2191-206. doi: 10.1038/sj.jid.5700849.

Segerman, A., et al. "There are Two Different Species B Adenovirus Receptors: sBAR, Common to Species BI andB2Adenoviruses, and sB2AR, Exclusively Used by Species B2 Adenoviruses" J Virol. Jan. 2003;77(2):1157-62. doi: 10.1128/jvi.77.2.1157-1162.2003.

Seppen, J., et al. "Lentivirus administration to rat muscle provides efficient sustained expression of erythropoietin," Blood. Aug. 1, 2001;98(3):594-6. doi: 10.1182/blood.v98.3.594.

Shayakhmetov, D. M., et al. "Dependence of Adenovirus Infectivity on Length of the Fiber Shaft Domain," 2000. JVirol 74: 10274-10286.

Shayakhmetov, D.M., et al. "Efficient Gene Transfer into Human CD341 Cells by a Retargeted Adenovirus Vector" J Virol. Mar. 2000;74(6):2567-83. doi: 10.1128/jvi.74.6.2567-2583.2000.

Short, J. J., et al. "Adenovirus serotype 3 utilizes CD80 (B 7 .1) and CD86 (B7.2) as cellular attachment receptors" Virology. May 1, 2004;322(2):349-59. doi: 10.1016/j.virol.2004.02.016.

Short, J. J., et al. "Members of adenovirus species B utilize CD80 and CD86 as cellular attachment receptors" Virus Res. Dec. 2006;122(1-2):144-53. doi: 10.1016/j.virusres.2006.07.009.

Signas, C., et al., "Adenovirus 3 Fiber Polypeptides Gene: Implications for the Structure of the Fiber Protein" J Virol. Feb. 1985;53(2):672-8. doi: 10.1128/JVI.53.2.672-678.1985.

Sirena, D., et al. "The human membrane cofactor CD46 is a receptor for species B adenovirus serotype 3" J Virol. May 2004;78(9):4454-62. doi: 10.1128/jvi.78.9.4454-4462.2004.

Sonoda, N., et al. "Clostridium perfringens Enterotoxin Fragment Removes Specific Claudins from Tight Junction Strands: Evidence for Direct Involvement of Claudins in Tight Junction Barrier" J Cell Biol. Oct. 4, 1999;147(1):195-204. doi: 10.1083/jcb_147.1.195.

Strauss, R., et al. "Analysis of Epithelial and Mesenchymal Markers in Ovarian Cancer Reveals Phenotypic Heterogeneity and Plasticity" PLoS One. Jan. 14, 2011;6(1):e16186. doi: 10.1371/journal.pone.0016186.

Strauss, R., et al. "Anatomical and physical barriers to tumor targeting with oncolytic adenoviruses in vivo" Curr Opin Mol Ther. Oct. 2009;11(5):513-22.

Strauss, R., et al. "Epithelial Phenotype Confers Resistance of Ovarian Cancer Cells to Oncolytic Adenoviruses" Cancer Res. Jun. 15, 2009;69(12):5115-25. doi: 10.1158/0008-5472.CAN-09-0645.

Sumida, S. M., et al. "Neutralizing Antibodies to Adenovirus Serotype 5 Vaccine Vectors are Directed Primarily against the Adenovirus Hexon Protein" J Immunol. Jun. 1, 2005;174(11):7179-85. doi: 10.4049/jimmunol.174.11.7179.

Supplementary European Search Report issued Jan. 11, 2022 in EP 19743793.

Tang, L., et al., "Genome and Bioinformatic Analysis of a HAdV-B14p1 Virus Isolated from a Baby with Pneumonia in Beijing, China" PLoS One. 2013;8(3):e60345. doi: 10.1371/journal.pone.0060345.

Tate, J. E., et al. "Outbreak of Severe Respiratory Disease Associated with Emergent Human Adenovirus Sero type 14 at a US Air Force Training Facility in 2007," J Infect Dis. May 15, 2009;199(10):1419-26. doi: 10.1086/598520.

Thiery, J. P., et al. "Complex networks orchestrate epithelial mesenchymal transitions" Nat Rev Mol Cell Biol. Feb. 2006;7(2):131-42. doi: 10.1038/nrm1835.

Thomas, M. A., et al. "Immunosuppression Enhances Oncolytic Adenovirus Replication and Antitumor Efficacy in the Syrian Hamster Model" Mol Ther. Oct. 2008;16(10):1665-73. doi: 10.1038/mt.2008.162.

Toso, J. F., et al. "MAGE-I-specific Precursor Cytotoxic T-Lymphocytes Present among Tumor-infiltrating Lymphocytes from a Patient with Breast Cancer: Characterization and Antigen-specific Activation" Cancer Res Jan. 1996 56:16-20.

Trei, J. S., et al., "Spread of Adenovirus to Geographically Dispersed Military Installations, May-Oct. 2007" Emerg Infect Dis. May 2010;16(5):769-75. doi: 10.3201/eid1605.091633.

Trinh, H. V., et al., "Avidity Binding of Human Adenovirus Serotypes 3 and 7 to the Membrane Cofactor CD46 Triggers Infection" J Virol. Feb. 2012;86(3):1623-37. doi: 10.1128/JVI.06181-11.

Trojan, L., et al. "Identification of Metastasis-associated Genes in Prostate Cancer by Genetic Profiling of Human Prostate Cancer Cell Lines" Anticancer Res. Jan.-Feb. 2005;25(1A):183-91.

Turley, E. A., et al. "Mechanisms of Disease: epithelial-mesenchymal transition does cellular plasticity fuel neoplastic progression?" Nat Clin Pract Oncol. May 2008;5(5):280-90. doi: 10.1038/ncponc1089.

(56)                    References Cited

OTHER PUBLICATIONS

Tuve, S., et al. "Combination of Tumor Site-Located CTL-Associated Antigen-4 Blockade and Systemic Regulatory T-Cell Depletion Induces Tumor-Destructive Immune Responses," Cancer Res. Jun. 15, 2007;67(12):5929-39. doi:10.1158/0008-5472.CAN-06-4296.

Tuve, S., et al. "Role of Cellular Heparan Sulfate Proteoglycans in Infection of Human Adenovirus Serotype 3 and 35" PLoS Pathog. Oct. 2008;4(10):e1000189. doi: 10.1371/journal.ppat.1000189.

Tuve, S., et al., "A New Group B Adenovirus Receptor is Expressed at High Levels on Human Stem and Tumor Cells," J Virol. Dec. 2006;80(24):12109-20. doi: 10.1128/JVI.01370-06.

Ueno, N. T., et al., "Targeting EGFR in Triple Negative Breast Cancer," J Cancer, May 2011;2:324-8. doi: 10.7150/ca.2.324.

Mllegas-Mendez, A et al., "In Vivo Delivery of Antigens by Adenovirus Dodecahedron Induces Cellular and Humoral Immune Responses to Elicit Anti tumor Immunity", Molecular Therapy, Academic Press, San Diego, Ca, US, vol. 18, No. 5, May 1, 2010 (May 1, 2010), pp. 1046-1053.

Vermeer, P. D., et al. "Segregation of receptor and ligand regulates activation of epithelial growth factor receptor" Nature. Mar. 20, 2003;422(6929):322-6. doi: 10.1038/nature01440.

UnitProt Accession No. P04501 accessed Oct. 16, 2014 at URL: uniprot.org/uniprot/P04501.

Villegas-Mendez, A., et al., "In Vivo Delivery of Antigens by Adenovirus Dodecahedron Induces Cellular and Humoral Immune Responses to Elicit Antitumor Immunity," Mol Ther. May 2010;18(5):1046-53. doi: 10.1038/ mt.2010.16.

Walters, R.W., et al. "Adenovirus Fiber Disrupts CAR-Mediated Intercellular Adhesion Allowing Virus Escape," Cell. Sep. 20, 2002;110(6):789-99. doi: 10.1016/s0092-8674(02)00912-1.

Wang Hongjie, et al., "Structural and Functional Studies on the Interaction of Adenovirus Fiber Knobs and Desmoglein 2", Journal of Virology, vol. 87, No. 21, Nov. 2013 (Nov. 2013), pp. 11346-11362.

Wang, H., et al. "A recombinant adenovirus type 35 fiber knob protein sensitizes lymphoma cells to rituximab therapy" Blood. Jan. 21, 2010;115(3):592-600. doi: 10.1182/blood-2009-05-222463.

Wang, H., et al. "Identification of CD46 Binding Sites within the Adenovirus Serotype 35 Fiber Knob" J Virol. Dec. 2007;81(23):12785-92. doi: 10.1128/JVI.01732-07.

Wang, H., et al. "In Vitro and In Vivo Properties of Adenovirus Vectors with Increased Affinity to CD46," J Virol. Nov. 2008;82(21):10567-79. doi: 10.1128/JVI.01308-08.

Wang, H., et al. "Receptor usage of a newly emergent adenovirus type 14," May 10, 2009;387(2):436-41. doi: 10.1016/j.virol.2009.02.034.

Wang, H., et al., "A New Human DSG2-Transgenic Mouse Model for Studying the Tropism andPathology of Human Adenoviruses" J Virol. Jun. 2012;86(11):6286-302. doi: 10.1128/JVI.00205-12.

Wang, Hongjie, et al. "Desmoglein 2 is a receptor for adenovirus serotypes 3, 7, 11 and 14", Nature Medicine, vol. 17, No. 1, Jan. 2011 (Jan. 2011), p. 96.

Wang, Hongjie, et al., "Multimerization of Adenovirus Serotype 3 Fiber Knob Domains is Required for Efficient Binding of Virus to Desmoglein 2 and Subsequent Opening of Epithelial Junctions", Journal of Virology, vol. 35, No. 13, Jul. 2011 (Jul. 2011), pp. 6390-6402.

Wheeler, D., et al. "Understanding resistance to EGFR inhibitors-impact on future treatment strategies," Nat Rev Clin Oncol. Sep. 2010;7(9):493-507. doi: 10.1038/nrclinonc.2010.97.

Wu, S., et al. "Bacteroides fragilis enterotoxin cleaves the zonula adherens protein, E-cadherin," Proc Natl Acad Sci U S A. Dec. 8, 1998;95(25):14979-84. doi: 10.1073/pnas.95.25.14979.

Yamamoto, M., et al. "Current Issues and Future Directions of Oncolytic Adenoviruses," Mol Ther. Feb. 2010;18 (2):243-50. doi: 10.1038/mt.2009.266.

Yang, S. W., et al. "Conditionally replicating adenovirus expressing TIMP2 for ovarian cancer therapy" Clin Cancer Res. Feb. 1, 2011;17(3):538-49. doi: 10.1158/1078-0432.CCR-10-1628.

Yang, Z., et al. "Development and Characterization of a Recombinant Madin-Darby Canine Kidney Cell Line That Expresses Rat Multidrug Resistance-Associate Protein I(rMRPI)," AAPS PharmSci. Mar. 9, 2004;6(1):E8. doi: 10.1208/os060108.

Yashiro, et al. "Decreased expression of the adhesion molecule desmolglein-2 is associated with diffuse-type gastric carcinoma," Eur J Cancer. Sep. 2006;42(14):2397-403. doi: 10.1016/j.ejca.2006.03.024.

Yeh, H.-Y., et al., "Human adenovirus type 41 contains two fibers" Virus Res. Aug. 1994;33(2):179-98. doi: 10.1016/0168-1702(94)90054-x.

Zeng, Y, et al. "A ligand-pseudoreceptor system based on de novo designed peptides for the generation of adenoviral vectors with altered tropism," J Gene Med. Apr. 2008;10(4):355-67. doi: 10.1002/jgm.1155.

Girouard, G., et al., "Adenovirus Serotype 14 Infection, New Brunswick, Canada, 2011," Emerg Infect Dis. Jan. 2013;19(1):119-22. doi: 10.3201/eid1901.120423.

Granio, O., et al. "Adenovirus 5-Fiber 35 Chimeric Vector Mediates Efficient Apical Correction of the Cystic Fibrosis Transmembrane Conductance Regulator Defect in Cystic Fibrosis Primary Airway Epithelia," Hum Gene Ther. Mar. 2010;21(3):251-69. doi: 10.1089/hum.2009.056.

Green, S. K., et al. "Disruption of Cell-Cell Adhesion Enhances Antibody-dependent Cellular Cytotoxicity: Implications for Antibody-based Therapeutics of Cancer" Cancer Res. Dec. 1, 2002;62(23):6891-900.

Guarino, M., et al. "Epithelial-mesenchymal transition and tumour invasion" Int J Biochem Cell Biol. 2007;39 (12):2153-60. doi: 10.1016/j.biocel.2007.07.011.

Gustafsson, D. J., et al. "The Arg279Glu Substitution in the Adenovirus Type I Ip (Adi Ip) Fiber Knob Abolishes EDTA-Resistant Binding to A549 and CHO-CD46 Cells, Converting the Phenotype to That of Ad7p" J Virol. Feb. 2006;80(4): 1897-905. doi: 10.1128/JVI.80.4.1897-1905.2006.

Harada, H., et al. "Abnormal Desmoglein Expression by Squamous Cell Carcinoma Cells" Acta Derm Venereol. Nov. 1996;76(6):417-20. doi: 10.2340/0001555576417420.

Harari, P. M., et al. "Biology of Interactions: Antiepidermal Growth Factor Receptor Agents," J Clin Oncol. Sep. 10, 2007;25(26):4057-65. doi: 10.1200/JCO.2007.11.8984.

Harper, B. W., et al. "Advances in Platinum Chemotherapeutics," Chemistry. Jun. 25, 2010;16(24):7064-77. doi: 10.1002/chem.201000148.

Hasegawa, K., et al., "Affinity Thresholds for Membrane Fusion Triggering by Viral Glycoproleins" J Virol. Dec. 2007;81(23):13149-57. doi: 10.1128/JVI.01415-07.

Hemminki, O., et al. "Preclinical and Clinical Data with a Fully Serotype 3 Oncolytic Adenovirus Ad3-hTERT-EIA in the Treatment of Advanced Solid Tumors" Molecular Therapy, May 2010, vol. 18, Supplement 1, S74, Article 193.

Hemminki, O., et al., "Ad3-hTERT-E1A, a Fully Serotype 3 Oncolytic Adenovirus, in Patients With Chemotherapy Refractory Cancer," Mol Ther. Sep. 2012;20(9):1821-30. doi: 10.1038/mt.2012.115.

Incardona, M.-F., et al., "EDNA: a framework for plugin-based applications applied to X-ray experiment online data analysis" Synchrotron Radiat. Nov. 2009;16(Pt 6):872-9. doi: 10.1107/S0909049509036681.

International Search Report issued Jan. 22, 2021 in PCT/US2020/054830.

International Search Report issued Jan. 30, 2014 in PCT/US2013/061431.

International Search Report issued Apr. 15, 2019 in PCT/US2019/01528.

International Search Report issued Oct. 10, 2011 in PCT/US2011/040053.

International Search Report issued Dec. 19, 2014 in PCT/US2014/057139.

Kabasch, W., "XDS" Acta Crystallogr D Biol Crystallogr. Feb. 2010;66(Pt 2):125-32. doi: 10.1107/S0907444909047337.

Kabsch, W., "Integration, scaling, space-group assignment and post-refinement" Acta Crystallogr D Biol Crystallogr. Feb. 2010;66(Pt 2):133-44. doi: 10.1107/S0907444909047374.

(56) References Cited

OTHER PUBLICATIONS

Kajon, A. E., et al., "Molecular Epidemiology and Brief History of Emerging Adenovirus 14-Associaled Respiratory Disease in the United States" The Journal of Infectious Diseases, vol. 202, Issue 1, Jul. 1, 2010, pp. 93-103, https://doi.org/10.1086/653083.

Kalin, S., et al. "Macropinocytic Uptake and Infection of Human Epithelial Cells with Species B2 Adenovirus Type 35" J Virol. May 2010;84(10):5336-50. doi: 10.1128/JVI.02494-09. Epub Mar. 17, 2010.

Karamouzis, M. V., et al. "Therapies Directed Against Epidermal Growth Factor Receptor in Aerodigestive Carcinomas" JAMA. Jul. 4, 2007;298(1):70-82. doi: 10.1001/jama.298.1.70.

Katz, J., et al. "Characterization of Porphyromonas gingivalis-Induced Degradation of Epithelial Cell Junctional Complexes" Infect Immun. Mar. 2000;68(3):1441-9. doi: 10.1128/IAI.68.3.1441-1449.2000.

Keim, S. A., et al. "Generation and Characterization of Monoclonal Antibodies Against the Proregion of Human Desmoglein-2" Hybridoma (Larchmt). Aug. 2008;27(4):249-58. doi: 10.1089/hyb.2008.0020.

Khatri, P., et al. "New Onto-Tools: Promoter-Express, nsSNPCounter and Onto-Translate," Nucleic Acids Res. Jul. 1, 2006;34(Web Server issue):W626-31. doi: 10.1093/nar/gkl213.

Kirby, I., et al. "Identification of Contact Residues and Definition of the CAR-Binding Site of Adenovirus Type 5 Fiber Protein" J Virol. Mar. 2000;74(6):2804-13. doi: 10.1128/jvi.74.6.2804-2813.2000.

Klessner, J. L., et al. "EGFR and ADAMs Cooperate to Regulate Shedding and Endocytic Trafficking of the Desmosomal Cadherin Desmoglein 2" Mol Biol Cell. Jan. 2009;20(1):328-37. doi: 10.1091/mbc.e08-04-0356.

Koeser, J., et al. "De novo formation of desmosomes in cultured cells upon transfection of genes encoding specific desmosomal components" 2003. Exp Cell Res 285:114-130.

Koski, A., et al. "Treatment of Cancer Patients With a Serotype 5/3 Chimeric Oncolytic Adenovirus Expressing GMCSF" Mol Ther. Oct. 2010;18(10):1874-84. doi: 10.1038/mt.2010.161.

Kowalczyk, A. P., et al., "Structure and function of desmosomal transmembrane core and plaque molecules" Biophys Chem. May 1994;50(1-2):97-112. doi: 10.1016/0301-4622(94)85023-2.

Kurzen, H., et al. "Expression of desmosomal proteins in squamous cell carcinomas of the skin" J Cutan Pathol. Nov. 2003;30(10):621-30. doi: 10.1034/j.1600-0560.2003.00122.x.

Larsen, M., al. et al "Phosphatases in cell-matrix adhesion and migration" Nat Rev Mol Cell Biol 4, 700-711 (2003). https://doi.org/10.1038/nrm1199.

Latorre, I. J., et al., "Viral oncoprotein-induced mislocalization of select PDZ proteins disrupts tight junctions and causes polarity defects in epithelial cells" J Cell Sci. Sep. 15, 2005;118(Pt 18):4283-93. doi: 10.1242/jcs.02560.

Lee, C., et al. "Targeting YB-1 in HER-2 Overexpressing Breast Cancer Cells Induces Apoptosis via the mTOR/STAT3 Pathway and Supresses Tumor Growth in Mice" Cancer Res. Nov. 1, 2008;68(21):8661-6. doi: 10.1158/0008-5472.CAN-08-1082.

Leopold, P. L., et al. "Intracellular trafficking of adenovirus: Many means to many ends," Adv Drug Deliv Rev. Aug. 10, 2007;59(8):810-21. doi: 10.1016/j.addr.2007.06.007.

Lesinak, D., et al. "beta1-Integrin Circumvents the Anti proliferative Effects of Trastuzumab in Human Epidermal Growth Factor Receptor-2-Positive Breast Cancer" Cancer Res. Nov. 15, 2009;69(22):8620-8. doi: 10.1158/0008-5472.CAN-09-1591.

Lewis, P. F., et al., "A Community-Based Outbreak of Severe Respiratory Illness Caused by Human Adenovirus Serotype 14" The Journal of Infectious Diseases, vol. 199, Issue 10, May 15, 2009, pp. 1427-1434, https://doi.org/10.1086/598521.

Li, J., et al. "Adenovirus fiber shaft contains a trimerization element that supports peptide fusion for targeted gene delivery" J Virol. Dec. 2006;80(24):12324-31. doi: 10.1128/JVI.01331-06.

Li, Z., et al. "Toward a stem cell gene therapy for breast cancer" Blood. May 28, 2009;113(22):5423-33. doi: 10.1182/blood-2008-10-187237.

Li, Z., et al. "Xenograft Models for Liver Metastasis: Relationship between Tumor Morphology and Adenovirus Vector Transduction" Mol Ther. May 2004;9(5):650-7. doi: 10.1016/j.ymthe.2004.01.021.

Litowski, J. R., et al. "Designing Heterodimeric Two-stranded-Helical Coiled-coils" J Pept Res. Dec. 2001;58(6):477-92. doi: 10.1034/j.1399-3011.2001.10972.x.

Lortat-Jacob, H., et al. "Kinetic Analysis of Adenovirus Fiber Binding to its Receptor Reveals an Avidity Mechanism for Trimeric ReceptorLigand Interactions" J Biol Chem. Mar. 23, 2001;276(12):9009-15. doi: 10.1074/jbc.M009304200.

Louie, J. K., et al. "Severe Pneumonia Due to Adenovirus Serotype 14: A New Respiratory Threat?" Clinical Infectious Diseases, vol. 46, Issue 3, Feb. 1, 2008, pp. 421-425, https://doi.org/10.1086/525261.

MMWR, "Acute Respiratory Disease Associated with Adenovirus Serotype 14—Four States, 2006-2007," Center for Disease Control, Nov. 16, 2007, 5 pages.

Mahoney, M. G., et al. "Interspecies conservation and differential expression of mouse desmoglein gene family," Exp Dermatol. Apr. 2002; 11(2):115-25. doi: 10.1034/j. 1600-0625.2002.

Marttila, M., et al. "CD46 is a Cellular Receptor for All Species B Adenoviruses except Types 3 and 7," J Virol. Nov. 2005;79(22):14429-36. doi: 10.1128/JVI.79.22.14429-14436.2005.

McCoy, A. J., et al., "Phaser crystallographic software" J Appl Crystallogr. Aug. 1, 2007;40(Pt 4):658-674. doi: 10.1107/S0021889807021206.

Mei, Y. F., et al., "Hemagglutination properties and nucleotide sequence analysis of the fiber gene of adenovirus genome types 11p and 11a" Virology. Jun. 1993; 194(2):453-62. doi: 10.1006/viro.1993.1284.

Metzgar, D. M., et al., "Abrupt Emergence of Diverse Species B Adenoviruses at US Military Recruit Training Centers" The Journal of Infectious Diseases, vol. 196, Issue 10, Nov. 15, 2007, pp. 1465-1473, https://doi.org/10.1086/522970.

* cited by examiner

Figure 1A
Serous
Clear
cell
endometroid
Figure 1B
Omentum
Pelvic
Small
Intestine
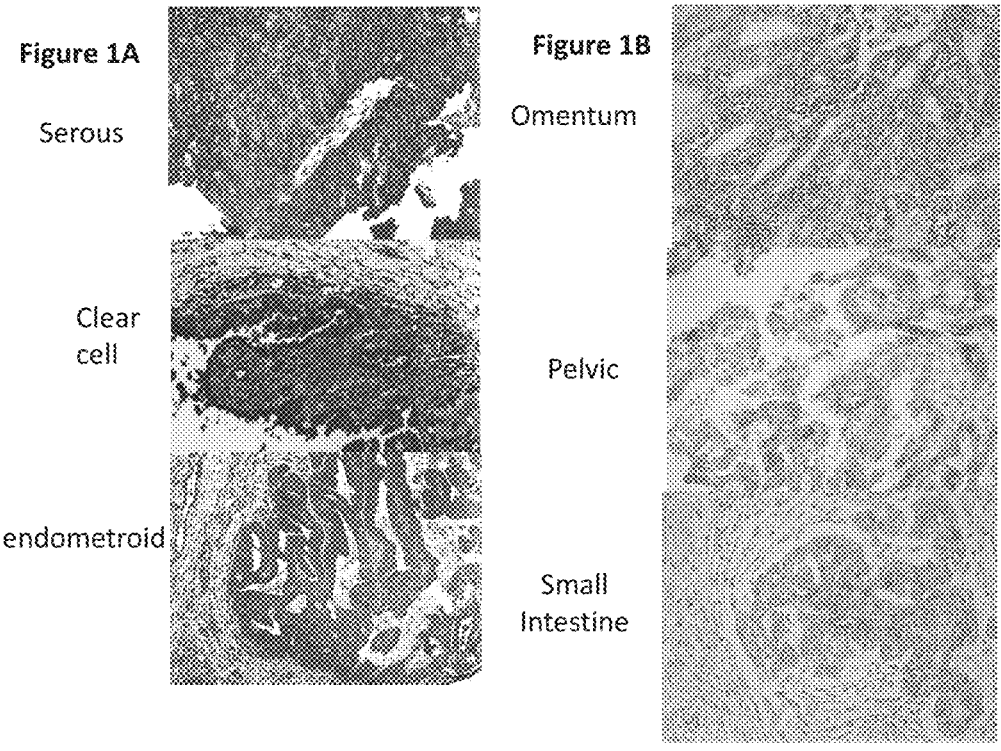
Figure 1C
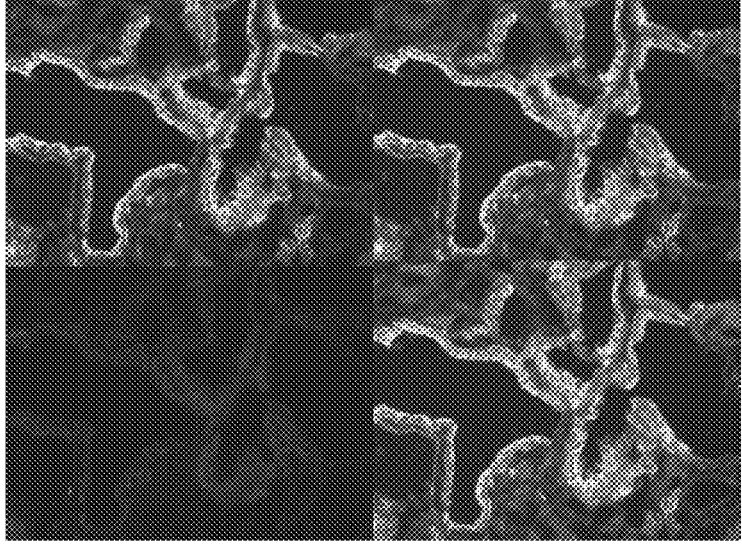
OVC316 labelled for DSG2(green),
claudin7(red)

Normal          Grade I          Grade II          Grade III

Figure 2B  n=33 n=34 n=46 n=89 p=0.013 p<0.001 p=0.360

Ratio DSG2+ to total area

Normal  1  2  3

Cancer Grade

Figure 2C   * * *** n=75 n=72 n=36 n=28

Ratio DSG2+ to total area

Mucinous  Serous  Metastatic  Normal

*** p<0.001 vs normal, Student's t-test

|           | Coefficient | P-value |
|-----------|-------------|---------|
| Intercept | 0.0830      | 0.0204  |
| Grade 1   | 0.0694      | 0.1660  |
| Grade 2   | 0.2739      | $1.71 \times 10^{-8}$ |
| Grade 3   | 0.3087      | $3.37 \times 10^{-12}$ |

Figure 3A   chemo-resistant                    chemo-sensitive

Figure 3B

Progression-Free Survival
Figure 4A
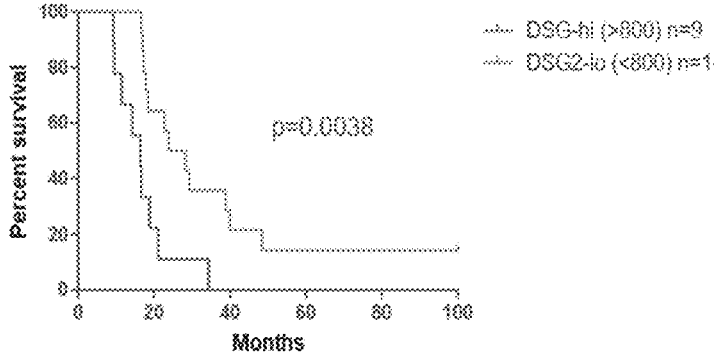
Survival
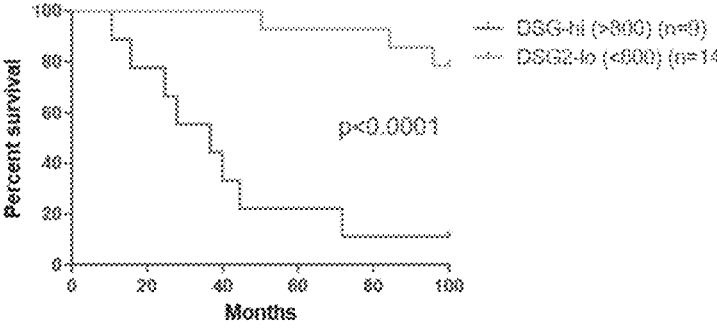
Figure 4B
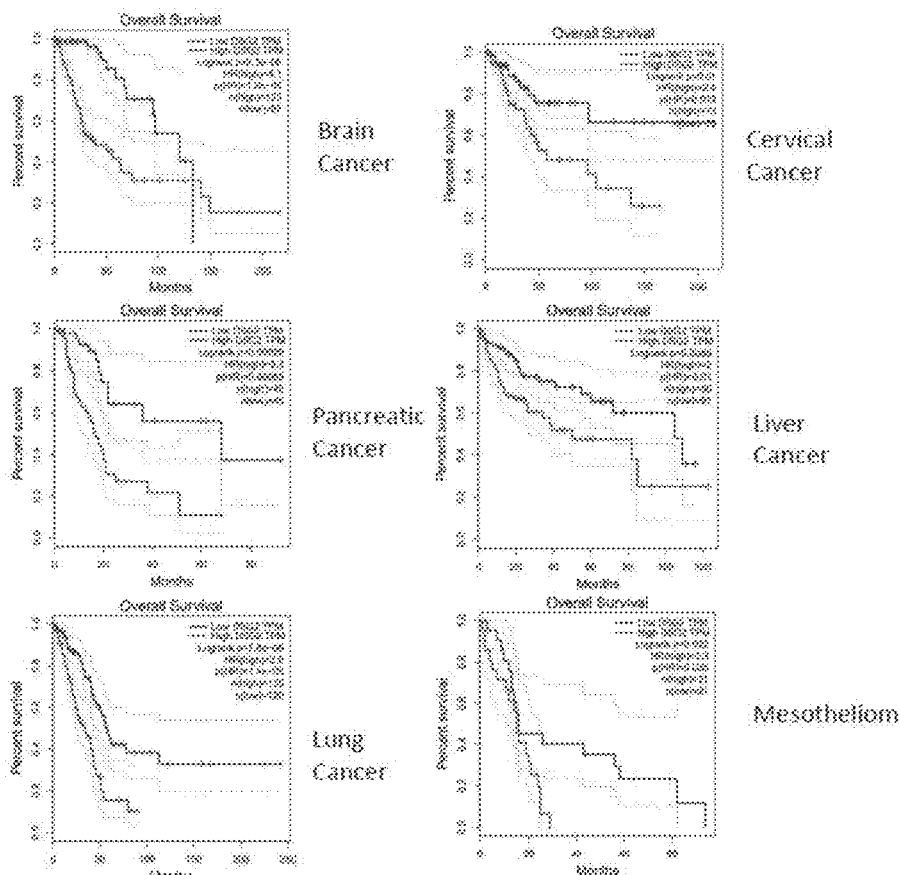

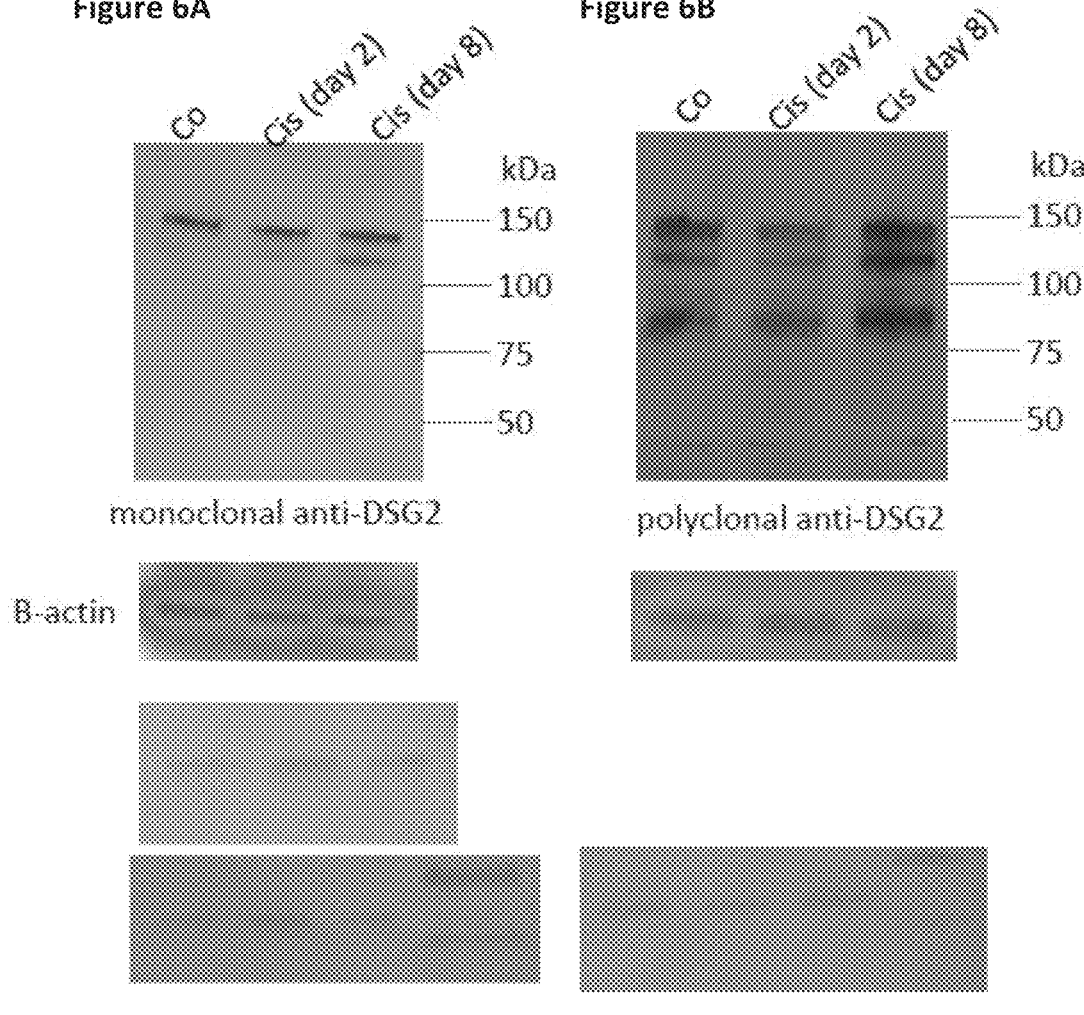

Pancreas

Breast

Small Cell
Lung

Stomach

DETECTION OF DESMOGLEIN-2 IN CANCERS OF EPITHELIAL ORIGIN

This application is a continuation of International Application No. PCT/US2020/054830, filed Oct. 8, 2020 which claims priority to U.S. Provisional Patent Application No. 62/913,071, filed on Oct. 9, 2019, which is herein incorporated by reference in its entirety.

STATEMENT OF GOVERNMENT INTEREST

This invention was made with Government support under R43 CA206607 awarded by The National Institute of Health. The government has certain rights in the invention.

BACKGROUND

Technical Field

The present invention relates generally to detection of desmoglein-2 in cancers of epithelial cell origin. More specifically, the invention relates to detection of desmoglein-2 expression in cancer and using this information to determine prognosis, treatment strategy, stage of the tumor, and whether the cancer is chemoresistant.

Description of the Related Art

Although mortality rates of many cancers, including ovarian, lung, prostate and breast cancer, have been falling over the last few decades, the incidence of cancer is still high. For example, ovarian cancer ranks the highest in terms of pathological burden of any cancer in the female reproductive tract. An estimated 22 530 diagnoses and 13 980 deaths will occur in the United States in 2019 (Key Statistics for Ovarian Cancer: American Cancer Society; 2018 [Available from: https://www.cancer.org/cancer/ovarian-cancer/about/key-statistics.htm]) representing a significant burden in women's health. Recent advances in novel cancer treatments such as checkpoint inhibitors hold promise, but a persistent problem in solid tumor therapy is the presence of physical barriers, which may act to prevent entry of immune cells and various forms of therapeutics including chemotherapy and radiotherapy.

Epithelial junctions are of particular interest in physical barrier formation, as the structure of a tight junction can be so tight as to exclude entry of particles as small as 400 Daltons (Anderson JM. Physiology. 2001; 16(3):126-30). These junctions are involved in the regulation of ion transport across epithelia, preservation of structural integrity and to exclude entry of microbes, or—in the case of tumors—therapeutics. Epithelial junctions are formed of multiple types of junctions, including tight junctions, desmosomes, gap junctions, and adherens junctions. Each of these junctions have specialized roles and may be all present on a specific cell-cell junction. Tight junctions, also called zonula occludens, are often found in locations where impermeability of soluble molecules is required, such as in the stomach and blood-brain barrier (4, 5).

Desmoglein-2 (DSG2) is a protein associated with desmosomes responsible for forming cell-to-cell junctions and as anchors for intermediate filaments. DSG2 has been commonly observed to be overexpressed in multiple types of cancer (Brennan and Mahoney Cell adhesion & migration. 2009; 3(2):148-54.), indicating that tumors take advantage of DSG2 overexpression as a means of forming tight physical barriers and contributing to resistance against chemotherapeutics. This makes DSG2 an appealing target, where its compromise in tumor cells would result in enhanced permeation or penetration of therapeutics and immune cells. In the context of ovarian cancer, data do not clearly point to a conclusive association with over-expression of DSG2 (Buckanovich et al., Journal of clinical oncology. 2007; 25(7):852-61). Previous examinations of DSG2 as a cancer biomarker have often been part of an omics-type approach of biomarker discovery, and DSG2 itself was mostly neglected for further study in favor of other epithelial proteins.

There thus remains a need in the art for use of DSG2 as a biomarker in ovarian cancer to indicate aggressiveness and/or therapeutic resistance and to correlate the levels of DSG2 expression with recurrence, metastasis, and survival.

All of the subject matter discussed in the Background section is not necessarily prior art and should not be assumed to be prior art merely as a result of its discussion in the Background section. Along these lines, any recognition of problems in the prior art discussed in the Background section or associated with such subject matter should not be treated as prior art unless expressly stated to be prior art. Instead, the discussion of any subject matter in the Background section should be treated as part of the inventor's approach to the particular problem, which in and of itself may also be inventive.

BRIEF SUMMARY OF INVENTION

In brief, the present disclosure provides methods of detecting a chemoresistant cancer in a patient, comprising, detecting elevated expression of desmoglein-2 (DSG-2) in a sample of the cancer, as compared to DSG-2 expression level from known chemosensitive cancers. In certain embodiments, the DSG-2 expression is detected by a DSG-2 binding reagent. DSG-2 binding reagents can be proteins, such as anti-DSG-2 antibodies, or aptamers, or polypeptides (engineered binding proteins), or inorganic matrices (molecular imprinted polymers).

In certain embodiments, the DSG-2 expression is measured by a quantitative mRNA technique, such as qPCR, or Northern blot analysis. In certain embodiments, elevated expression is an mRNA read of greater than 800 in qPCR. In other embodiments, the DSG-2 binding reagent is used to stain a histology slide of ovarian cancer. In yet other embodiments, the DSG-2 binding reagent is used in a quantitative ELISA, or the DSG-2 binding reagent may be used to stain a Western blot.

The disclosure also provides methods for predicting the stage and survival time of subject suffering from a cancer comprising the steps of, determining an expression level of DSG-2 in a tumor sample obtained from the subject, comparing the expression level in the tumor sample with a threshold value, and concluding what stage of cancer that the subject has and that the subject will have a shorter survival time depending on the expression level of DSG-2.

The disclosure also provides methods for determining whether a subject suffering from a cancer will respond to certain treatment regimens, comprising, determining an expression level of DSG-2 in a tumor sample obtained from the subject, comparing the expression level of the tumor sample with a threshold value, and concluding that the subject will be refractory to treatment depending on the expression level of DSG-2.

In certain embodiments, the treatment regimen is an anthracycline/platinum-based combination, in other embodiments, the treatment comprises a DSG2 binding reagent, such as one derived from an adenovirus. In particular embodiments, the treatment itself is an adenovirus. In other embodiments, the DSG2 binding reagent is a junction opener. In certain embodiments, the cancer is ovarian cancer.

The above-mentioned and additional features of the present invention and the manner of obtaining them will become apparent, and the invention will be best understood by reference to the following more detailed description. All references disclosed herein are hereby incorporated by reference in their entirety as if each was incorporated individually.

This Brief Summary has been provided to introduce certain concepts in a simplified form that are further described in detail below in the Detailed Description. Except where otherwise expressly stated, this Brief Summary is not intended to identify key or essential features of the claimed subject matter, nor is it intended to limit the scope of the claimed subject matter.

The details of one or more embodiments are set forth in the description below. The features illustrated or described in connection with one exemplary embodiment may be combined with the features of other embodiments. Thus, any of the various embodiments described herein can be combined to provide further embodiments. Aspects of the embodiments can be modified, if necessary, to employ concepts of the various patents, applications and publications as identified herein to provide yet further embodiments. Other features, objects and advantages will be apparent from the description, the drawings, and the claims.

BRIEF DESCRIPTION OF THE DRAWINGS

Exemplary features of the present disclosure, its nature and various advantages will be apparent from the accompanying drawings and the following detailed description of various embodiments. Non-limiting and non-exhaustive embodiments are described with reference to the accompanying drawings, wherein like labels or reference numbers refer to like parts throughout the various views unless otherwise specified. The sizes and relative positions of elements in the drawings are not necessarily drawn to scale. For example, the shapes of various elements are selected, enlarged, and positioned to improve drawing legibility. The particular shapes of the elements as drawn have been selected for ease of recognition in the drawings. One or more embodiments are described hereinafter with reference to the accompanying drawings in which:

FIG. 1A shows clinical samples of serous, clear cell, and endometroid tumors stained for DSG2 using a commercially available DSG2 antibody and hematoxylin/eosin counterstain.

FIG. 1B shows clinical samples of metastases at the omentum, pelvis, and small intestine of ovarian origin stained for DSG2, with hematoxylin/eosin counterstain.

FIG. 1C shows OVC316 cells, a primary ovarian cancer cell line, stained for DSG2 and claudin7 with secondary antibodies conjugated to FITC (DSG2) or PE (claudin7).

FIG. 2B shows a numerical comparison of DSG2 staining by grade from 0 (normal) to 3. DSG2 staining intensity was quantified using Visiopharm software. P-values represent statistical significance determined with pairwise comparisons using the Student's t-test. Error bars indicate 95% confidence intervals.

FIG. 2C shows numerical comparison of DSG2 staining by classification of cell type. Error bars indicate 95% confidence intervals.

FIG. 3A shows DSG2 protein expression in tissue samples from patients classified as chemo-resistant or chemo-sensitive. Samples were stained for DSG2 using immunohistochemistry techniques.

FIG. 3B shows DSG2 mRNA expression levels in a cohort of ovarian cancer patients (n=49) classified as chemosensitive or chemoresistant. DSG2 mRNA reads were quantified by RNAseq and for each point totaled all DSG2 reads for a tumor sample as detected by RNAseq.

FIG. 4A depicts the correlation of DSG2 expression to ovarian cancer progression-free survival (PFS) and general survival. These results are from a cohort of ovarian cancer patients from the Fred Hutchinson Cancer Center (Seattle, WA) placed into DSG-high or DSG-low expressing groups as defined by a threshold of DSG2 mRNA read of 800. Analyses were done for months of PFS and general survival, using the Log-Rank (Mantel-Cox) tests for comparisons between populations. As seen in the survival graph about 80% of patients with low DSG2 expression were alive at the end of the study, while only about 10% of patients that were DSG2 high were alive.

FIG. 4B shows analyses of overall survival of cancer cohorts in The Cancer Genome Atlas (TCGA). In this set of data, "DSG2-high" and "DSG2-low" were defined as being above and below the number of median message copies for DSG2 expression level. For each graph the tumor type is indicated. P-values are results of the Log-Rank test for comparison of survival between populations. N-values are the number of patients in each group.

FIG. 5A shows the effect of DSG2 expression in response to cisplatin. Ovarian cancer cells (OV-CAR) were subject to cisplatin treatment, and cell supernatants were subsequently blotted for DSG2 expression using the Western Blot protocol, in the case where the lysates were run in native state.

FIG. 5B shows the effect of DSG2 expression in response to cisplatin. Ovarian cancer cells (OV-CAR) were subject to cisplatin treatment, and cell supernatants were subsequently blotted for DSG2 expression using the Western Blot protocol, in the case where lysates were boiled for 10 minutes prior to blotting, where samples were tested for DSG2 protein on days 1,2,3,6 after treatment. The full length DSG2 band at around 120-130 kDa indicates the precursor to the shed, cleaved version at about 80 kDa.

FIG. 5C shows protein amounts on blots that were quantified using ImageJ and compared by fold difference of band intensity, using day 0 (pre-treatment) as a control.

FIG. 6A shows results when cell supernatants used in FIG. 5A were pre-tested with monoclonal antibodies to confirm specificity of antibodies used against DSG2 in the cell supernatant. Antibodies for housekeeping β-actin protein were used as a negative control.

FIG. 6B shows results when cell supernatant used in FIG. 5A were pretested with polyclonal antibodies to confirm specificity of antibodies used against DSG2 in the cell supernatant. Antibodies for housekeeping β-actin protein were used as a negative control.

Figure 7:
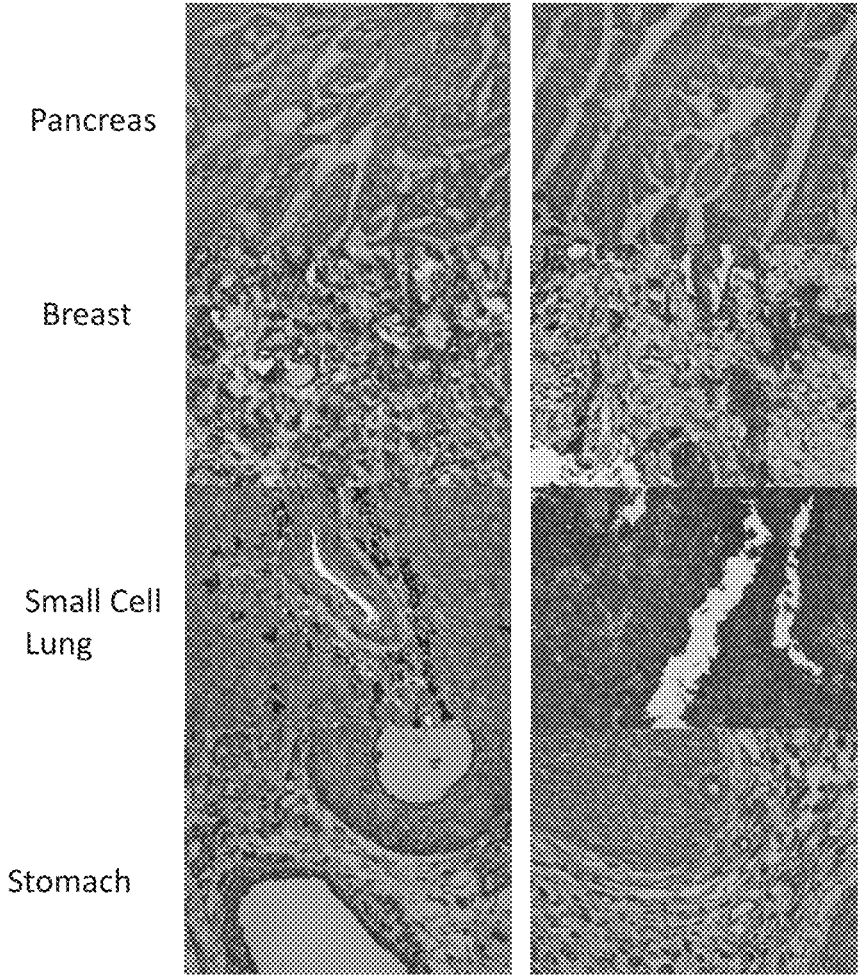

FIG. 7 shows expression of DSG2 in various cancers. Clinical tissue samples from other primary cancers with sites as indicated were stained for DSG2 using immunohisto-chemistry procedures.

Figure 8A:
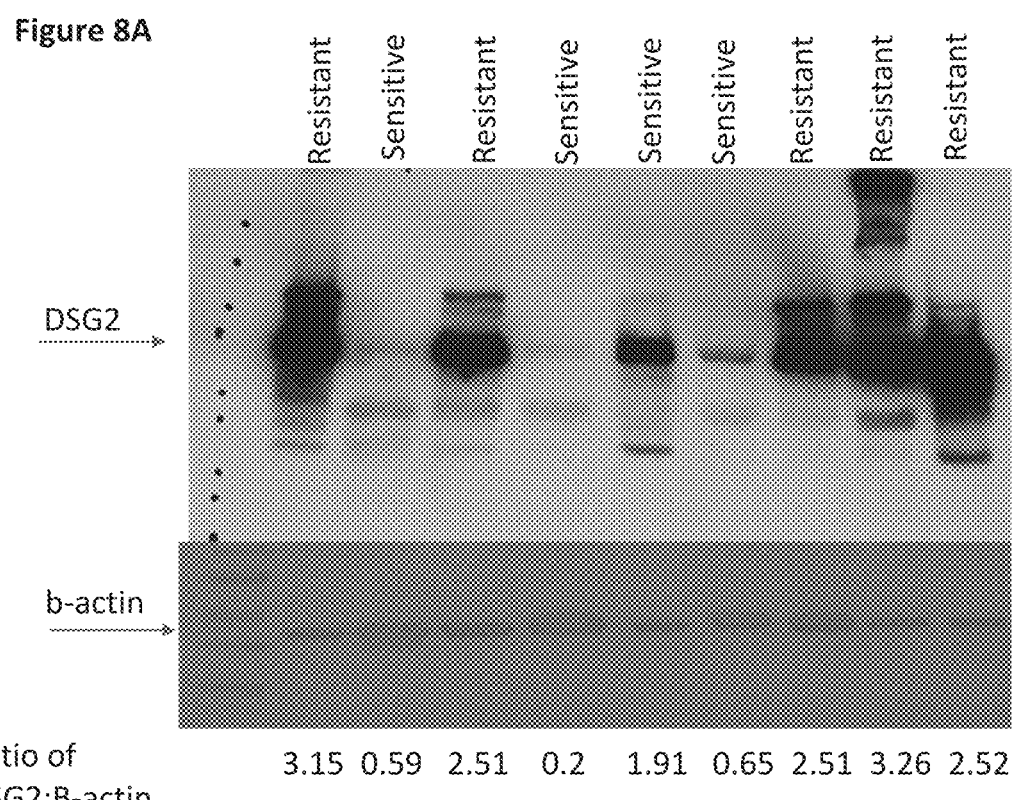

FIG. 8A shows a DSG2 Western blot of biopsy lysates from chemo-resistant or chemo-sensitive patients. A set of representative samples are shown.

Figure 8B:
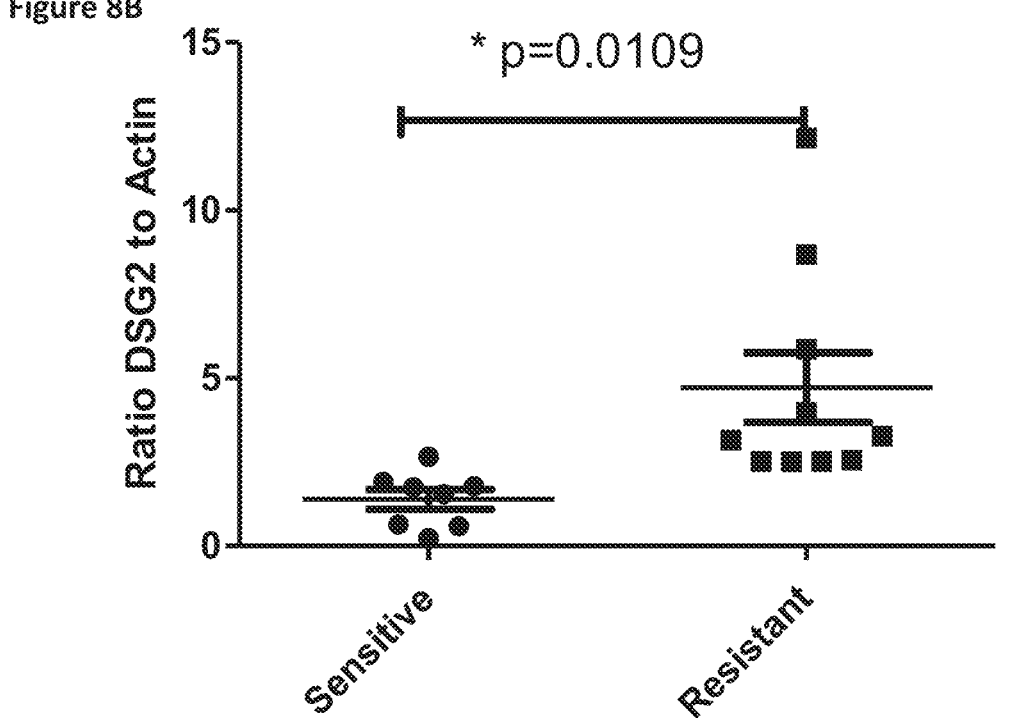

FIG. 8B shows normalized DSG2 Western blot signals, where n=18.

DETAILED DESCRIPTION

The present invention may be understood more readily by reference to the following detailed description of preferred embodiments of the invention and the Examples included herein. In reading this detailed description, and unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. The term "comprises" means "includes." The abbreviation, "e.g." is derived from the Latin exempli gratia, and is used herein to indicate a non-limiting example. Thus, the abbreviation "e.g." is synonymous with the term "for example."

This disclosure provides for use of DSG2 expression as a biomarker for cancer and as a companion diagnostic for DSG2 targeting therapeutic strategies. In particular, high expression is often associated with higher grade, chemoresistance, shorter time of progression-free survival (PFS), and shorter time of general survival. Particularly striking is the difference in PFS and general survival between DSG2-low and DSG2-high expressing populations, seen in two separate cohorts, underscoring the utility of use of DSG2 expression levels as a prognostic indicator for survival of e.g. ovarian cancer patients.

Desmoglein-2 (DSG) may be detected in tissues by any of a variety of methods and techniques. Expression of protein may be detected, e.g., by anti-DSG2 antibody staining of tissue sections, by anti-DSG2 antibody staining on isolated cells, by ELISA on cell supernatants or cell lysates, and by Western blot. Antibodies may be polyclonal, monoclonal, single chain (e.g., scFv), or a chimera of an antibody binding site with another protein or carrier molecule. Antibodies may be procured from commercial sources or generated. Methods and techniques to raise and construct antibodies are well known.

Non-antibody reagents may also be used. For examples, such reagents may be aptamers, polypeptides (engineered binding proteins), and inorganic matrices (molecular imprinted polymers).

The antibody and non-antibody reagents (collectively called binding reagents) should preferentially detect (bind to) DSG2, and may detect more than one form of DSG2. Binding reagents may detect full-length DSG2, the extra-cellular domain, intracellular domain, natural cleavage products. In some embodiments, specific detection of one or another form of DSG2 will be advantageous. For example, it may be preferable to detect a soluble form as opposed to a cell membrane form. In some embodiments, the binding reagents may be conjugated with a directly detectable reagent, such as a dye by spectrophotometric methods (e.g., colorimetry), fluorescent and chemiluminescent molecules, radioactive molecule, etc. In other embodiments, a second reagent, which is labeled, detects the DSG2 binding reagent. Second reagents include antibodies that detect the anti-DSG2 antibody.

As an alternative to, or in addition to detection of DSG2 protein, certain embodiments employ methods and techniques that detect mRNA expression of DSG2. A suitable method is RNA-Seq. Other suitable methods include rt-PCR, qPCR, Northern blot, Nanostring technology (Tsang et al., Expert Rev Mol Diagn. 2017 January; 17(1):95-103. Epub 2016 Dec. 12. Review), and single-cell RNA sequencing.

Expression of DSG2 is determined by any of the methods and techniques described herein and, for each patient sample, is scored as either high or low expression. High protein expression is established by analysis of antibody and non-antibody reagent binding to DSG2 as compared to normal controls.

When RNASeq is used in ovarian cancer, high expression of DSG2 is determined as at least on the order of 800 reads although in other cohorts and using different methodologies this level may change by sample preparation or sensitivity of detection. This level of expression is significantly increased compared to chemo-sensitive tumor control.

In some embodiments, a kit to detect DSG2 expression is provided. A kit to detect protein expression may include an antibody or non-antibody reagent that binds DSG2. If needed, a detecting reagent (e.g., antibody to the anti-DSG2 binding reagent) is included. Developing reagents to visu-alize the binding reaction may also be included.

Identification of patients predicted to have chemoresistant ovarian tumors has important implications for treatment of the tumor and for counselling the patient. High expression of DSG2 is indicative (correlates) of a tumor that is chemo-resistant (refractory) to first-line treatment, typically involv-ing an anthracycline/platinum-based combination. Further-more, patients' tumors with high levels of DSG2 expression may have a poorer prognosis, including a shorter time of progression-free survival (PFS), and shorter time of general survival although in some tumor types this trend may be reversed.

Approaches to treatment protocols may be different for patients with chemoresistant tumors than for patients with chemosensitive tumors. For example, patients with high levels of DSG2 expression may be guided to enroll in experimental trials or treated with very aggressive strategies early on. Alternatively, or as an adjunct to traditional treat-ment, the DSG2 protein itself may be targeted with anti-bodies, specific medications, or constructs designed to down regulate expression of DSG2. In an exemplary protocol, an engineered form of the Ad3 knob, the junction-opener (JO) protein, has been used to target cancers expressing DSG2 as it causes shedding of DSG2 from the surfaces of cells, causing a transient opening of tight junctions to facilitate entry of therapeutics (Lu et al. PLoS pathogens. 2013; 9(10):e1003718). As a result of the JO-mediated junction opening, chemotherapeutics (including paclitaxel and doxo-rubicin-based therapies) and monoclonal antibodies co-ad-ministered with JO showed higher efficacy in delaying tumor growth in multiple xenograft models involving breast and lung cancer cell lines (see for example, Beyer, et al., Cancer research. 2011; 71(22):7080-90). In addition, differ-ent treatment protocols, perhaps including additional or alternative chemotherapeutics to the commonly used ones, may be used.

FIGS. 1A, 1B and 1C (collectively FIGS. 1A-1C) show staining of DSG2 in various tissues, where: FIG. 1A provides three images showing clinical samples of serous (top image), clear cell (middle image), and endometroid (bottom image) tumors stained for DSG2 using a commercially available DSG2 antibody and hematoxylin/eosin counterstain; FIG. 18 provides three images showing clinical samples of metastases at the omentum (top image), pelvis (middle image), and small intestine (lower image) of ovarian origin stained for DSG2, with hematoxylin/eosin counterstain; and FIG. C shows OVC316 cells, a primary ovarian cancer cell line, stained for DSG2 and claudin7 with secondary antibodies conjugated to FITC (DSG2) or PE (claudin7).

In FIG. 1C there are four panels, each showing the same image of the primary ovarian cancer cell line, but with different staining. In the upper left image, bright staining on the surface of tumor cells for DSG2 is seen in these ovarian cancer cells indicating prominent overexpression of DSG2. In the upper right image, overlay of DSG2 stain and Claudin7 show the relationship between desmoglein and claudin in these cells. In the lower left image, muted staining of the ovarian cancer cells for Claudin7, a protein thought to interact with DSG2, shows localization of this protein in ovarian tumor cells. In the lower right image, overlay of DSG2, Claudin7 and a nuclear dye show the relationship of the proteins in individualized cells and their nuclei.

Figures 2A, 2D:
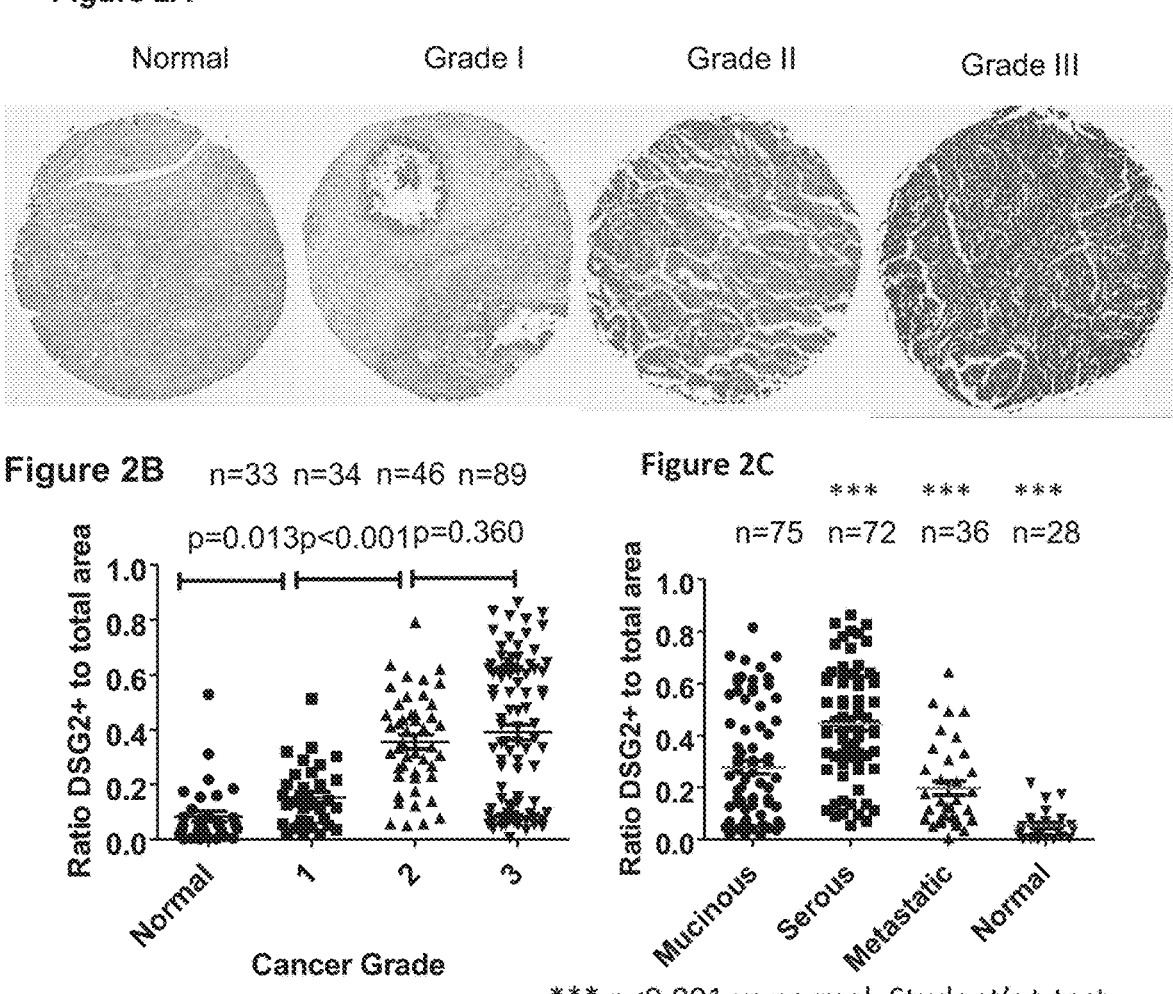
FIG. 2A shows representative DSG2 stains of different ovarian cancer tissue classified by grade, from normal to grade 3.
FIG. 2D shows coefficient and p-values for linear regression modelling of DSG2+ ratio by grade, using normal grade as base. Coefficient and p-value with null hypothesis of coefficient=0 is shown. *** indicates p-value of <0.001 when compared to normal ratios, using the unpaired Student's t-test.

FIGS. 2A, 2B, 2C and 2D (collectively FIGS. 2A-2D) provide information about expression of DSG2 in various ovarian cancers. Commercially available ovarian cancer tissue panels were stained for DSG2 and analyzed for staining intensity, where: FIG. 2A shows representative DSG2 stains of different ovarian cancer tissue classified by grade, from (moving left to right) normal to grade I (or 1), to grade II (or 2), to grade III (or 3); FIG. 2B shows a numerical comparison of DSG2 staining by grade from 0 (normal) to 3. DSG2 staining intensity was quantified using Visiopharm software. P-values represent statistical significance determined with pairwise comparisons using the Student's t-test. Error bars indicate 95% confidence intervals; FIG. 2C shows numerical comparison of DSG2 staining by classification of cell type. Error bars indicate 95% confidence intervals; and FIG. 2D provides a Table showing coefficient and p-values for linear regression modelling of DSG2+ ratio by grade, using normal grade as base. Coefficient and p-value with null hypothesis of coefficient=0 is shown. *** indicates p-value of <0.001 when compared to normal ratios, using the unpaired Student's t-test. In the Table, Intercept has a coefficient of 0.0830 and a p-value of 0.0204; Grade 1 has a coefficient of 0.0694 and a p-value of 0.1660; Grade 2 has a coefficient of 0.2739 and a p-value of $1.71 \times 10^{-8}$, and Grade 3 has a coefficient of 0.3087 and a p-value of $3.37 \times 10^{-12}$.

Figures 3A, 3B:
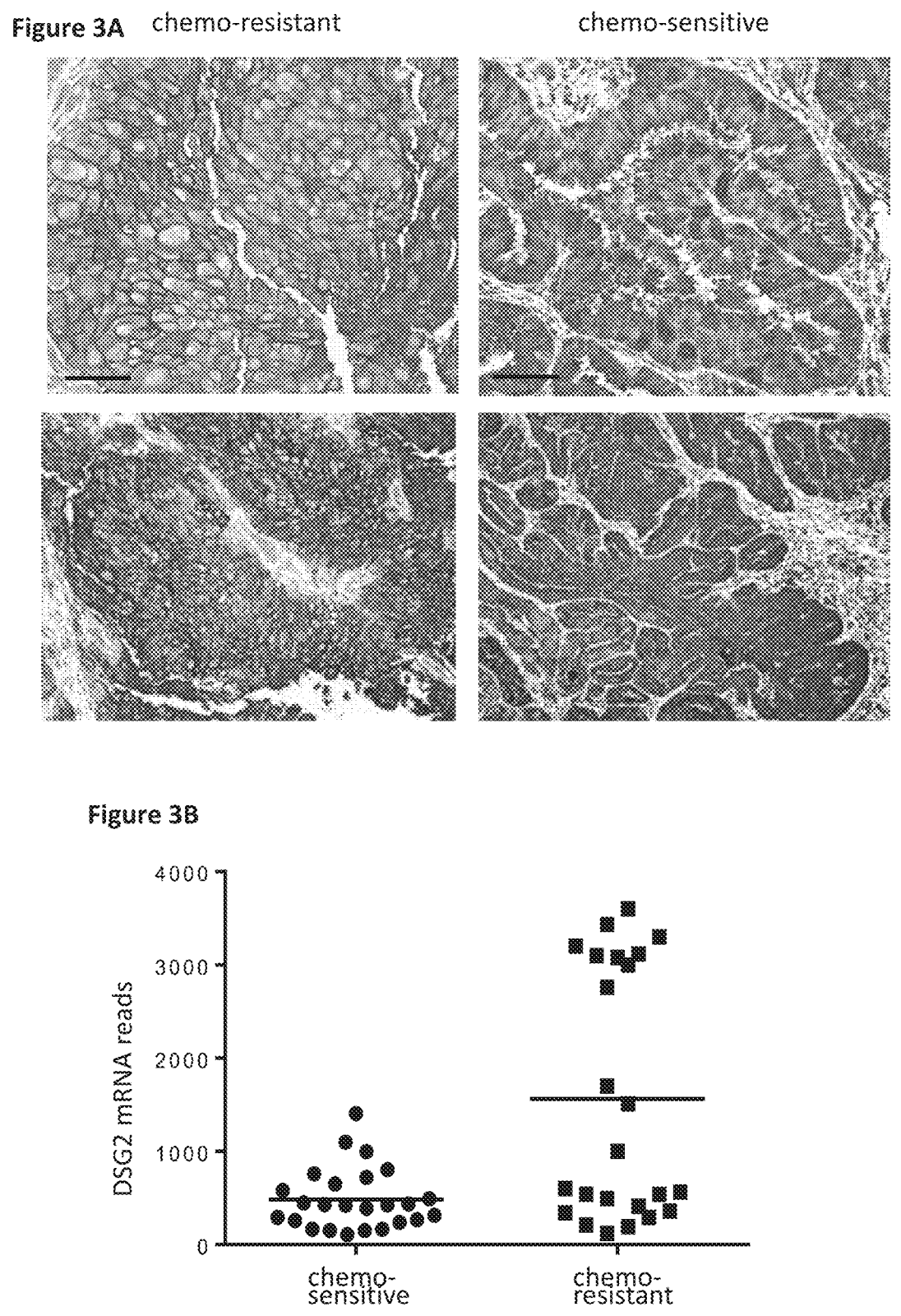

FIGS. 3A and 3B (collectively FIGS. 3A-3B) show results of DSG2 expression in chemosensitive and chemoresistant tumors, where: FIG. 3A shows DSG2 protein expression in four tissue samples from patients classified as chemo-resistant (two images of tissue, one above the other, both on the left) or chemo-sensitive (two images of tissue, one above the other, both on the right). Samples were stained for DSG2 using immunohistochemistry techniques; and FIG. 3B shows DSG2 mRNA expression levels in a cohort of ovarian cancer patients (n=49) classified as chemosensitive or chemoresistant. DSG2 mRNA reads were quantified by RNAseq and for each point totaled all DSG2 reads for a tumor sample as detected by RNAseq.

FIGS. 4A and 4B (collectively FIGS. 4A-4B) show survival rates and progression-free survival in a number of tumors, where: FIG. 4A provides an upper and a lower panel, which depict the correlation of DSG2 expression to ovarian cancer progression-free survival (PFS) in the upper panel, and general survival in the lower panel. These results are from a cohort of ovarian cancer patients from the Fred Hutchinson Cancer Center (Seattle, WA) placed into DSG-high or DSG-low expressing groups as defined by a threshold of DSG2 mRNA read of 800. Analyses were done for months of PFS and general survival, using the Log-Rank (Mantel-Cox) tests for comparisons between populations. As seen in the survival graph about 80% of patients with low DSG2 expression were alive at the end of the study, while only about 10% of patients that were DSG2 high were alive; and FIG. 4B shows analyses of overall survival of cancer cohorts in The Cancer Genome Atlas (TCGA). In this set of data, "DSG2-high" and "DSG2-low" were defined as being above and below the number of median message copies for DSG2 expression level. For each of the six graphs provide in FIG. 4B the tumor type is indicated (the six tumor types being brain cancer, pancreatic cancer, lung cancer, cervical cancer, liver cancer, and mesothelioma). P-values are results of the Log-Rank test for comparison of survival between populations. N-values are the number of patients in each group.

Figure 5A:
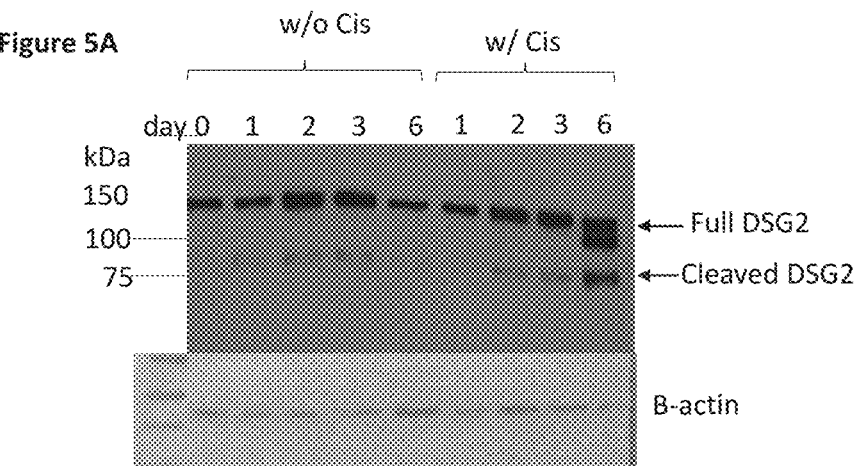
FIGS. 5A, 5B, and 5C show the effect of DSG2 expression in response to cisplatin. Ovarian cancer cells (OV-CAR) were subject to cisplatin treatment, and cell supernatants were subsequently blotted for DSG2 expression using the Western Blot protocol, where.
Figure 5B:
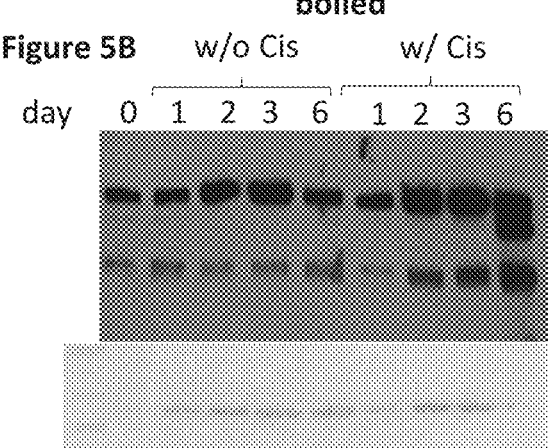
Figure 5C:
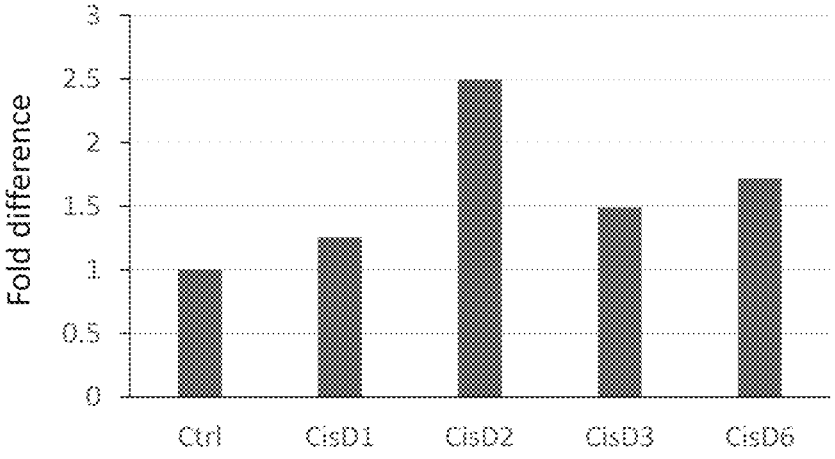

FIGS. 5A, 5B and 5C (collectively FIGS. 5A-5C) show the effect of DSG2 expression in response to cisplatin. Ovarian cancer cells (OV-CAR) were subject to cisplatin treatment, and cell supernatants were subsequently blotted for DSG2 expression using the Western Blot protocol, where: FIG. 5A shows results when lysates were run in native state; FIG. 5B shows results when lysates were boiled for 10 minutes prior to blotting, where samples were tested for DSG2 protein on days 1,2,3,6 after treatment. The full length DSG2 band at around 120-130 kDa indicates the precursor to the shed, cleaved version at about 80 kDa; and FIG. 5C shows protein amounts on the blots that were quantified using ImageJ and compared by fold difference of band intensity, using day 0 (pre-treatment) as a control.

FIGS. 6A and 6B (collectively FIGS. 6A-6B) display detection of antibodies to DSG2 after cisplatin treatment, where: FIG. 6A shows results when cell supernatants used in FIG. 4A were pre-tested with monoclonal antibodies to confirm specificity of antibodies used against DSG2 in the cell supernatant. Antibodies for housekeeping β-actin protein were used as a negative control; and FIG. 6B shows results when cell supernatant used in FIG. 4A were pretested with polyclonal antibodies to confirm specificity of antibodies used against DSG2 in the cell supernatant. Antibodies for housekeeping f-actin protein were used as a negative control.

FIG. 7 shows expression of DSG2 in various cancers. Clinical tissue samples from other primary cancers with sites as indicated were stained for DSG2 using immunohistochemistry procedures.

FIGS. 8A and 8B (collectively FIGS. 8A-8B) are Western blots, where: FIG. 8A shows a DSG2 Western blot of biopsy lysates from chemo-resistant or chemo-sensitive patients. A set of representative samples are shown; and FIG. 8B shows normalized DSG2 Western blot signals, where n=18.

The following are some exemplary numbered embodiments of the present disclosure.

1) A method of detecting a chemoresistant cancer in a patient, comprising:
   (a) detecting elevated expression of desmoglein-2 (DSG-2) in a sample of the cancer, as compared to DSG-2 expression level from known chemosensitive cancers.

2) The method of embodiment 1, wherein the DSG-2 expression is detected by a DSG-2 binding reagent.

3) The method of embodiment 1, wherein the DSG-2 expression is measured by a quantitative mRNA technique.

4) The method of embodiment 2, wherein the DSG-2 binding reagent is used to stain a histology slide of the cancer.

5) The method of embodiment 2, wherein the DSG-2 binding reagent is used in a quantitative ELISA.

6) The method of embodiment 2, wherein the DSG-2 binding reagent is used to stain a Western blot.

7) The method of any of embodiments 2-6, wherein the DSG-2 binding reagent is an anti-DSG2 antibody.

8) The method of embodiment 3, wherein the technique is qPCR.

9) The method of embodiment 3, wherein the technique is Northern blot analysis.

10) The method of embodiment 3, wherein elevated expression is an mRNA read of greater than 800.

11) A method for predicting the survival time of subject suffering from a cancer comprising the steps of
   i) determining an expression level of DSG-2 in a tumor sample obtained from the subject,
   ii) comparing the expression level in the tumor sample with a threshold value, and
   iii) concluding that the subject will have a short survival time depending on the expression level of DSG-2.

12) A method for determining whether a subject suffering from a cancer will respond to certain treatment regimens, comprising
   i) determining an expression level of DSG-2 in a tumor sample obtained from the subject,
   ii) comparing the expression level of the tumor sample with a threshold value, and
   iii) concluding that the subject will be refractory to treatment depending on the expression level of DSG-2.

13) The method of embodiment 12, wherein the treatment regimen is an anthracycline/platinum-based combination.

14) The method of embodiment 12, wherein the cancer is ovarian cancer.

15) The method of embodiment 12, wherein the treatment comprises a DSG-2 binding reagent.

16) The method of embodiment 15, wherein the DSG-2 binding reagent is from an adenovirus.

17) A method of embodiment 16, wherein the treatment itself is an adenovirus.

18) A method of embodiment 15, wherein the DSG-2 binding reagent is a junction opener.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In case of conflict, the present specification, including explanations of terms, will control. In addition, all the materials, methods, and examples are illustrative and not intended to be limiting.

It is also to be understood that as used herein and in the appended claims, the singular forms "a," "an," and "the" include plural reference unless the context clearly dictates otherwise, the term "X and/or Y" means "X" or "Y" or both "X" and "Y", and the letter "s" following a noun designates both the plural and singular forms of that noun. In addition, where features or aspects of the invention are described in terms of Markush groups, it is intended, and those skilled in the art will recognize, that the invention embraces and is also thereby described in terms of any individual member and any subgroup of members of the Markush group, and Applicants reserve the right to revise the application or claims to refer specifically to any individual member or any subgroup of members of the Markush group.

The following Examples are offered by way of illustration and not by way of limitation.

EXAMPLE 1

General Techniques Employed in the Examples

Antibodies. The following antibodies are used: mouse mAb anti-DSG2 (clone 6D8) (Cell Sciences, Canton, MA), mouse mAb anti-DSG2 (clone AH12.2) (Santa Cruz Biotechnology Inc, Santa Cruz, CA), polyclonal anti-DSG2 antibody (AF947) (R&D System), anti-proDSG2 (clone 20G1) (provided by James K. Wahl III, University of Nebraska Medical Center (13), rabbit mAb anti-p38 (clone D13E1, Cell Signaling Technology, Danvers, MA), rabbit mAb anti-pp38 (clone D3F9, Cell Signaling Technology, Danvers, MA), polyclonal rabbit anti-ADAM17 antibody (Millipore), mouse mAb anti-beta actin (clone Ac-74, Sigma).

Western Blot. Mini-PROTEAN precast gels (BIO-RAD, Hercules, CA) with 4-15% gradient polyacrylamide are used. A total of 1 μg protein mixed with 2× loading buffer (10 mM Tris-HCl, pH 6.8, 200 mM DTT, 4% SDS, 20% glycerol, 0.2% bromophenol blue) is loaded per lane. Samples are either boiled (B) for 5 min or loaded unboiled (UB). The following running buffer is used: 25 mM Tris, pH 8.3, 0.192 M glycine, 0.1% SDS. After electrophoresis, proteins are transferred to nitrocellulose and incubated with the corresponding antibodies. For detection of DSG2 binding, filters are incubated with recombinant human DSG2 protein and anti-DSG2 antibody 6D8 as described (Wang et al. Nat Med. 2011; 17(1):96-104). Other Western blots use a primary mouse monoclonal antibody followed by an anti-mouse IgG HRP conjugate. Selected Western blots are scanned and quantified using the ImageJ 1.32 software (National Institutes of Health, Bethesda, MD).

Immunohistochemistry staining for DSG2. Immunohistochemistry slides obtained from Fred Hutchinson Cancer Research Center are deparaffinized and hydrated through immersion in xylene, decreasing concentrations of ethanol (100%-95%-80%-70%), and water. Slides are then immersed in 0.3% hydrogen peroxide, followed by an additional rinse of water. Slides are then placed in 1% Unmasking solution (Vector Labs, Burlingame, CA) and placed in a miniature autoclave (going up to 125° C. for 1 hour). Slides are then incubated in 2.5% normal horse serum blocking solution (Vector Labs, Burlingame, CA) for 20 minutes at room temperature. Sections are then incubated in the primary antibody (goat anti-human DSG2, Abcam, Cambridge, UK) overnight at 4° C. Following an additional wash in PBS, 4 drops of ImmPRESS (Vector Labs, Burlingame, CA) are added and allowed to develop for around 5 minutes before washing with water. Sections are counterstained with Mayer's Hematoxylin (Sigma-Aldrich, St. Louis, MO) for 60 minutes, washed with water, and placed in PBS until development of a blue color. After the slides dry, 3-5 drops of VectaMount (Vector Labs, Burlingame, CA) are added to the slide with a cover slip placed on top and viewed under a microscope.

Immunofluorescence Staining of DSG2. OVC316 cells are fixed on a slide with a solution of 4% paraformaldehyde for 15 minutes at room temperature, then rinsed with PBS three times. The slide is then placed in blocking buffer (2% non-fat milk in PBS) for 60 minutes at room temperature. Primary antibodies anti-DSG2 (6D8, Abcam, UK) and anti-Claudin7 (ab27487, Abcam, UK) are prepared at a 1:1:50 dilution in PBS. Blocking solution is removed and slides are incubated with primary antibody overnight at 4° C. Slides are then washed with PBS three times and incubated with the secondary antibody mix (FITC-goat-anti-mouse Ab, PE-goat-anti-rabbit Ab) for 1 hour at room temperature in the dark. After incubation, slides are washed with PBS three times before mounting with Vectashield Antifade Mounting Medium+DAPI (Vector Labs, Burlingame, CA) viewing under a microscope with fluorescent filters.

DSG2 ELISA. ELISA is performed using a goat polyclonal anti-DSG2 antibody (R&D Systems, Minneapolis, MN) and the mouse monoclonal antibody 6D8 directed against ECD3 (AbD Serotec, Raleigh, NC). The detection limit of the DSG2 ELISA is 0.5 ng/ml.

mRNA quantification. Clinical blood samples from ovarian cancer patients were used for RNAseq at the Fred Hutchinson Sequencing Core. The total number of DSG2 copies detected are used for subsequent analyses. DSG2 levels are stratified as high or low based on the threshold of 800 reads (for the Fred Hutch samples) or as being above or below the median number found in the total patient population. (Cancer Atlas NIH data).

Clinical Samples and Statistical Analyses. All samples were collected in accordance with ethics protocols in place at Fred Hutchinson Cancer Research Center and University of Washington. Survival data on 23 ovarian cancer patients were collected with DSG2 levels taken upon surgery by qRT-PCR, with continued monitoring for recurrence. Another cohort of patients (n=49) was classified based on chemoresistance, defined as refractory to first-line treatment (involving an anthracycline/platinum-based combination). Cancer Genome Atlas (TCGA) data on DSG2 expression was available for an ovarian cancer cohort (National Institutes of Health, Bethesda, MD). Statistical analyses are carried out using Graphpad Prism (San Diego, CA, USA).

EXAMPLE 2

DSG2 is Overexpressed in Ovarian Cancer Primary and Metastatic Tissue with Loss of Cellular Polarization In this Example, a series of ovarian cancer tissue slides were stained for DSG2 by immunohistochemistry. Tissue sections of ovarian primary cancer tissue of serous, clear cell, and endometroid origin were stained using a commercially available DSG2 antibody and hematoxylin/eosin counterstain. (FIG. 1A) The staining showed localization of DSG2 was highest at the cell-cell junctions, as expected, although a more scattered distribution of DSG2 staining was present in contrast to normal tissue. Metastatic tissue showed similar expression patterns toward the edges of the tissue with relatively more uniform distribution throughout the core of the tumor (FIG. 18). FIGS. 1A and 1B show how the tumor related sections are darker brown (more DSG2) than the surrounding healthy tissue. Immunofluorescence staining of an ovarian cancer cell line, OVC316, showed abundant DSG2 staining toward the edges of the tissue (FIG. 1C). FIG. 1C shows how bright (large amounts of DSG2) a cancer is for this marker. These data indicate that DSG2 expression in ovarian cancer tissue of primary, metastatic, and cell line origins is not confined to the upper epithelial layers as predicted, but is also expressed in the core of the tumor and may also be scattered throughout cancerous tissue.

EXAMPLE 3

DSG2 is Differentially Expressed in Chemo-Resistant Ovarian Cancer

In this Example, DSG2 expression is evaluated in ovarian cancer cells that are chemo-resistant and in cells that are chemo-sensitive.

First, commercially available ovarian cancer tissue panels were stained for DSG2 and analyzed for staining intensity. FIG. 2A shows representative DSG2 stains of different ovarian cancer tissue classified by grade, from normal to grade 3. The higher the grade of ovarian cancer, the more DSG2 is expressed. FIG. 2B shows numerical comparison of DSG2 staining from grade 0 (normal) to grade 3. DSG2 staining intensity was quantified using Visiopharm software. P-values represent statistical significance determined with pairwise comparisons using the Student's t-test. Error bars indicate 95% confidence intervals. The quantitative data mirror the visual staining in FIG. 2A. Numerical comparison of DSG2 staining by classification of cell type is shown in FIG. 2C. Error bars indicate 95% confidence intervals. FIG. 2D presents coefficient and p-values for linear regression modelling of DSG2+ ratio by grade, using normal grade as base. Coefficient and p-value with null hypothesis of coefficient=0 is shown. *** indicates p-value of <0.001 when compared to normal ratios, using the unpaired Student's t-test.

Tissue sections of ovarian tumor samples were obtained from patients classified as chemo-resistant (defined as refractory to the first-line treatment of ovarian cancer) or chemo-sensitive (see Example 1). The sections were stained by the immunostaining technique described in Example 1. As shown in FIG. 3A, DSG2 expression in chemo-resistant ovarian cancer displays higher expression, as evidenced by darker staining and a more uniform distribution throughout the entire tumor. Notably, cell morphology was more disordered in the chemo-resistant tumors, with abnormally shaped and abnormally distributed DSG2+ cells penetrating the tumor throughout.

Chemo-resistant cancer tissue also showed higher expression of DSG2 mRNA when compared to chemo-susceptible tissue. As shown in FIG. 38, when analyzed by RNAseq, chemo-resistant patients showed on average significantly higher reads of DSG2 mRNA. Interestingly, within the DSG2-hi population a clustering of two distinct populations occurred, indicating high DSG2 expression is partially associated, but not solely responsible factor with chemo-resistance. Importantly, high DSG2 expression wasn't detected in any of the samples from chemo-sensitive tumors. Thus, DSG2 may be associated with the occurrence and mediation of chemo-resistance in ovarian cancer.

EXAMPLE 4

DSG2 Expression Correlates to Survival of Patients with Cancer

In this Example, the correlation of DSG2 expression to survival is established. A cohort of 23 ovarian cancer patients were classified as DSG2-high (>800 copies DSG2 mRNA) or DSG2-low (<800 copies). Survival and progression-free survival of this cohort was analyzed. As shown in FIG. 4A, the DSG2-high ("DSG-2-hi") patients had a significantly shorter regression free survival (p=0.0038) and general survival (p<0.0001) than DSG2-low ("DSG2-lo") patients. The average time until progression was markedly different in the two groups, with 50% of the DSG2-high population having a progression-free survival (PFS) of only 16 months vs 26 months in the DSG2-low population. These data were further corroborated by public data from a larger sample of cancer patients from the Cancer Genome Atlas Program, where similar correlations were observed.

In certain non-ovarian cancers DSG2-high expressing patients again had statistically significant shorter general survival when compared to DSG2-low expressing patients (FIG. 4B). Certain cancers showed the opposite trend, but for many cancer DSG2 is a significant marker of prognosis either good or bad depending on the tumor type. The drastic difference in survival and progression in cancer patients highlights the importance of DSG2 in mediating chemo-resistance and faster progression and the value and effectiveness of DSG2 to be used as a prognostic to predict patient outcomes. For the tumor types shown, a clear relationship between survival and DSG2 expression is present.

EXAMPLE 5

DSG2 is Upregulated in Cancer in Response to Cisplatin-Based Treatment

In this Example, a potential mode of chemoresistance was investigated, DSG2 protein levels were determined in cancer cells after treatment with cisplatin, a commonly used platinum-based therapeutic used as first-line treatment of ovarian cancer and its metastases.

Cell supernatants from ovarian cancer cell lines (OV-CAR) were first interrogated with monoclonal and polyclonal anti-DSG2 antibodies to confirm specificity of the antibodies. Monoclonal antibodies showed superior specificity to full-size precursor DSG2 and cleaved DSG2 (FIGS. 5A, 5B, 5C, 6A and 6B); monoclonal antibodies were used for subsequent analyses. Within 2 days of cisplatin treatment, the presence of cleaved DSG2, a product of DSG2 shedding, was detected in cell supernatant (FIGS. 5A and 5B). Quantitative analysis of the blot intensity indicated DSG2 peaking at 2 days after cisplatin treatment. These results indicate that DSG2 is upregulated and shed in increased amounts in ovarian cancer cells in response to cisplatin treatment, implicating DSG2 as one of the responsive mechanisms of ovarian cancer to platinum-based chemotherapeutics such as cisplatin.

EXAMPLE 6

Expression of DSG2 in a Variety of Cancers

Clinical tissue samples from other primary cancers were stained for DSG2 using immunohistochemistry methods of Example 1. FIG. 7 shows that DSG2 is highly expressed in a variety of cancer types. Similarly, FIG. 4 demonstrates that DSG2 expression is modulated in a large variety of cancers.

EXAMPLE 7

Expression of DSG2 by Western Blot

Western blots of biopsy lysates are evaluated for DSG2 expression. FIG. 8A show DSG2 Western blot of biopsy lysates from chemo-resistant or chemo-sensitive patients. A set of representative samples are shown. FIG. 8B presents normalized DSG2 Western blot signals from 18 tumor samples. The data show that DSG2 protein expression is substantially higher in chemo-resistant tumors.

All references disclosed herein, including patent references and non-patent references, are hereby incorporated by reference in their entirety as if each was incorporated individually.

It is to be understood that the terminology used herein is for the purpose of describing specific embodiments only and is not intended to be limiting. It is further to be understood that unless specifically defined herein, the terminology used herein is to be given its traditional meaning as known in the relevant art.

Reference throughout this specification to "one embodiment" or "an embodiment" and variations thereof means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents, i.e., one or more, unless the content and context clearly dictates otherwise. It should also be noted that the conjunctive terms, "and" and "or" are generally employed in the broadest sense to include "and/or" unless the content and context clearly dictates inclusivity or exclusivity as the case may be. Thus, the use of the alternative (e.g., "or") should be understood to mean either one, both, or any combination thereof of the alternatives. In addition, the composition of "and" and "or" when recited herein as "and/or" is intended to encompass an embodiment that includes all of the associated items or ideas and one or more other alternative embodiments that include fewer than all of the associated items or ideas.

Unless the context requires otherwise, throughout the specification and claims that follow, the word "comprise" and synonyms and variants thereof such as "have" and "include", as well as variations thereof such as "comprises" and "comprising" are to be construed in an open, inclusive sense, e.g., "including, but not limited to." The term "consisting essentially of" limits the scope of a claim to the specified materials or steps, or to those that do not materially affect the basic and novel characteristics of the claimed invention.

Any headings used within this document are only being utilized to expedite its review by the reader, and should not be construed as limiting the invention or claims in any manner. Thus, the headings and Abstract of the Disclosure provided herein are for convenience only and do not interpret the scope or meaning of the embodiments.

Where a range of values is provided herein, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

For example, any concentration range, percentage range, ratio range, or integer range provided herein is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means±20% of the indicated range, value, or structure, unless otherwise indicated.

All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Such documents may be incorporated by reference for the purpose of describing and disclosing, for example, materials and methodologies described in the publications, which might be used in connection with the presently described invention. The publications discussed above and throughout the text are provided solely for their disclosure prior to the filing date of the present application. Nothing herein is to be construed as an admission that the inventors are not entitled to antedate any referenced publication by virtue of prior invention.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

Furthermore, the written description portion of this patent includes all claims. Furthermore, all claims, including all original claims as well as all claims from any and all priority documents, are hereby incorporated by reference in their entirety into the written description portion of the specification, and Applicants reserve the right to physically incorporate into the written description or any other portion of the application, any and all such claims. Thus, for example, under no circumstances may the patent be interpreted as allegedly not providing a written description for a claim on the assertion that the precise wording of the claim is not set forth in haec verba in written description portion of the patent.

The claims will be interpreted according to law. However, and notwithstanding the alleged or perceived ease or difficulty of interpreting any claim or portion thereof, under no circumstances may any adjustment or amendment of a claim or any portion thereof during prosecution of the application or applications leading to this patent be interpreted as having forfeited any right to any and all equivalents thereof that do not form a part of the prior art.

Other nonlimiting embodiments are within the following claims. The patent may not be interpreted to be limited to the specific examples or nonlimiting embodiments or methods specifically and/or expressly disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The invention claimed is:

1. A method of treating a subject suffering from a chemo-resistant ovarian cancer, the method comprising:
   obtaining an ovarian cancer sample from the subject;
   detecting desmoglein-2 (DSG-2) expression in the ovarian cancer sample obtained from the subject;
   diagnosing the chemo-resistant ovarian cancer in the subject, wherein a higher amount of DSG-2 expression in the ovarian cancer sample following a treatment with one or more chemotherapeutic agents relative to DSG-2 expression in an ovarian cancer sample obtained from the subject prior to the treatment indicates that the ovarian cancer is chemo-resistant;
   administering to the subject an effective amount of a DSG-2 binding reagent, wherein the DSG-2 binding reagent comprises a junction opener; and
   administering the one or more chemotherapeutic agents.

2. The method of claim 1, wherein the one or more chemotherapeutic agents comprise an anthracycline/platinum-based combination.

3. The method of claim 1, wherein the DSG-2 binding reagent is from an adenovirus.

4. The method of claim 1, further comprising, determining the amount of DSG-2 expression in the ovarian cancer sample by RNAseq.

5. The method of claim 1, further comprising, determining the amount of DSG-2 expression in the ovarian cancer sample by Western blot.

6. The method of claim 1, further comprising, determining the amount of DSG-2 expression in the ovarian cancer sample by reverse transcription polymerase chain reaction (RT-PCR).

7. The method of claim 1, further comprising, determining the amount of DSG-2 expression in the ovarian cancer sample by a quantitative ELISA.

8. The method of claim 1, further comprising, determining the amount of DSG-2 expression in the ovarian cancer sample by staining the ovarian cancer sample with anti-DSG2 antibody.

9. The method of claim 1, further comprising, determining the amount of DSG-2 expression in the ovarian cancer sample by detecting an amount of a DSG-2 binding reagent bound to the DSG-2 in the ovarian sample, wherein the DSG-2 binding reagent is conjugated to a dye, a fluorescent molecule or a chemiluminescence molecule.

10. The method of claim 9, wherein the DSG-2 binding reagent comprises an anti-DSG2 antibody.

11. The method of claim 9, wherein the DSG-2 binding reagent comprises a junction opener.

* * * * *